US009547748B2

(12) United States Patent
Jiang et al.

(10) Patent No.: US 9,547,748 B2
(45) Date of Patent: Jan. 17, 2017

(54) METHOD FOR DETERMINING FETAL CHROMOSOMAL ABNORMALITY

(75) Inventors: Fuman Jiang, Shenzhen (CN); Huifei Chen, Shenzhen (CN); Xianghua Chai, Shenzhen (CN); Yuying Yuan, Shenzhen (CN); Xiuqing Zhang, Shenzhen (CN); Fang Chen, Shenzhen (CN)

(73) Assignee: BGI HEALTH SERVICE CO., LTD., Shenzhen, Guangdong (CN)

( * ) Notice: Subject to any disclaimer, the term of this patent is extended or adjusted under 35 U.S.C. 154(b) by 0 days.

(21) Appl. No.: 13/641,080

(22) PCT Filed: Jun. 29, 2011

(86) PCT No.: PCT/CN2011/001070
§ 371 (c)(1),
(2), (4) Date: Oct. 12, 2012

(87) PCT Pub. No.: WO2013/000100
PCT Pub. Date: Jan. 3, 2013

(65) Prior Publication Data
US 2014/0099642 A1   Apr. 10, 2014

(51) Int. Cl.
*G06F 19/00* (2011.01)
*G06F 19/18* (2011.01)
*C12Q 1/68* (2006.01)
*G06F 19/22* (2011.01)

(52) U.S. Cl.
CPC ............ *G06F 19/18* (2013.01); *C12Q 1/6883* (2013.01); *C12Q 2600/156* (2013.01); *G06F 19/22* (2013.01)

(58) Field of Classification Search
None
See application file for complete search history.

(56) References Cited

U.S. PATENT DOCUMENTS

| | | |
|---|---|---|
| 6,251,638 B1 | 6/2001 | Umansky et al. |
| 6,258,540 B1 | 7/2001 | Lo et al. |
| 6,287,820 B1 | 9/2001 | Umansky et al. |
| 6,492,144 B1 | 12/2002 | Umansky et al. |
| RE39,920 E | 11/2007 | Umansky et al. |
| 7,799,531 B2 | 9/2010 | Mitchell et al. |
| 7,838,647 B2 | 11/2010 | Hahn et al. |
| 2001/0051341 A1 | 12/2001 | Lo et al. |
| 2002/0119478 A1 | 8/2002 | Umansky et al. |
| 2005/0164241 A1 | 7/2005 | Hahn et al. |
| 2006/0046258 A1 | 3/2006 | Lapidus et al. |
| 2007/0087345 A1 | 4/2007 | Olson-Munoz et al. |
| 2007/0202525 A1 | 8/2007 | Quake et al. |
| 2008/0026390 A1 | 1/2008 | Stoughton et al. |
| 2008/0038733 A1 | 2/2008 | Bischoff et al. |
| 2008/0050739 A1 | 2/2008 | Stoughton et al. |
| 2008/0070792 A1 | 3/2008 | Stoughton et al. |
| 2008/0090239 A1 | 4/2008 | Shoemaker et al. |
| 2008/0113358 A1 | 5/2008 | Kapur et al. |
| 2008/0124721 A1 | 5/2008 | Fuchs et al. |
| 2008/0138809 A1 | 6/2008 | Kapur et al. |
| 2008/0176237 A1 | 7/2008 | Bhatt et al. |
| 2008/0220422 A1 | 9/2008 | Shoemaker et al. |
| 2009/0029377 A1 | 1/2009 | Lo et al. |
| 2009/0087847 A1 | 4/2009 | Lo et al. |
| 2009/0170113 A1 | 7/2009 | Quake et al. |
| 2009/0170114 A1 | 7/2009 | Quake et al. |
| 2009/0280492 A1 | 11/2009 | Stoughton et al. |
| 2009/0291443 A1 | 11/2009 | Stoughton et al. |
| 2010/0112575 A1 | 5/2010 | Fan et al. |
| 2010/0112586 A1 | 5/2010 | Stoughton et al. |
| 2010/0112590 A1 | 5/2010 | Lo et al. |
| 2010/0124751 A1 | 5/2010 | Quake et al. |
| 2010/0124752 A1 | 5/2010 | Quake et al. |
| 2010/0136529 A1 | 6/2010 | Shoemaker et al. |
| 2010/0138165 A1 | 6/2010 | Fan et al. |
| 2010/0184043 A1 | 7/2010 | Mitchell et al. |
| 2010/0184044 A1 | 7/2010 | Mitchell et al. |
| 2010/0216151 A1 | 8/2010 | Lapidus et al. |

(Continued)

FOREIGN PATENT DOCUMENTS

| | | |
|---|---|---|
| AU | 727919 | 9/1998 |
| AU | 2012261664 | 1/2013 |

(Continued)

OTHER PUBLICATIONS

Aksglaede et al., "Abnormal Sex Chromosome Constitution and Longitudinal Growth: Serum Levels of Insulin-Like Growth Factor (IGF)-I, IGF Binding Protein-3, Luteinizing Hormone, and Testosterone in 109 Males with 47,XXY, 47,XYY, or Sex-Determining Region of the Y Chromosome (SRY)-Positive 46,XX Karyotypes," J. Clin. Endocrinol. Metab. (2008) 93(1):169-176.
Birke, "Shape Constrained Kernel Density Estimation," Journal of Statistical Planning and Inference (2008) 136(8):2851-2862.
Bock (1993) "Understanding Klinefelter Syndrome: A Guide for XXY Males and Their Families," NIH Pub. No. 93/3202.
Chiu et al., "Noninvasive Prenatal Diagnosis of Fetal Chromosomal Aneuploidy by Massively Parallel Genomic Sequencing of DNA in Maternal Plasma," Proc. Natl. Acad. Sci USA (2008) 105:20458-20463.
Dear, "One by One: Single Molecule Tools for Genomics," Briefings in Functional Genomics and Proteomics (2003) 1(4):397-416.
Driscoll et al., "Clinical Practice. Prenatal Screening for Aneuploidy," N. Engl. J. Med. (2009) 360:2556-2562.

(Continued)

*Primary Examiner* — Pablo S Whaley
(74) *Attorney, Agent, or Firm* — Morrison & Foerster LLP

(57) ABSTRACT

The current invention is directed to methods for noninvasive detection of fetal genetic abnormalities by large-scale sequencing of nucleotides from maternal biological sample. Further provided are methods to remove GC bias from the sequencing results according to the difference in GC content of a chromosome. The current invention not only makes the detection much more accurate but also represents a comprehensive method for fetal aneuploidy detection including sex chromosome disorders such as XO, XXX, XXY, and XYY, etc.

28 Claims, 17 Drawing Sheets

(56) References Cited

U.S. PATENT DOCUMENTS

| | | | |
|---|---|---|---|
| 2010/0216153 A1* | 8/2010 | Lapidus et al. | 435/6 |
| 2010/0255492 A1 | 10/2010 | Quake et al. | |
| 2010/0255493 A1 | 10/2010 | Quake et al. | |
| 2010/0256013 A1 | 10/2010 | Quake et al. | |
| 2010/0261188 A1 | 10/2010 | Bhatt et al. | |
| 2010/0291571 A1 | 11/2010 | Stoughton et al. | |
| 2010/0291572 A1 | 11/2010 | Stoughton et al. | |
| 2011/0319272 A1* | 12/2011 | Fan et al. | 506/2 |

FOREIGN PATENT DOCUMENTS

| | | |
|---|---|---|
| CA | 2 791 118 | 12/2012 |
| CN | 101675169 | 3/2010 |
| CN | 101849236 | 9/2010 |
| CN | 103403183 | 11/2013 |
| EP | 0 994 963 | 5/2003 |
| EP | 2 561 103 | 8/2014 |
| JP | 5659319 | 12/2014 |
| SG | 191757 | 8/2013 |
| WO | WO-2007/092473 | 8/2007 |

OTHER PUBLICATIONS

Fan et al., "Noninvasive Diagnosis of Fetal Aneuploidy by Shotgun Sequencing DNA from Maternal Blood," Proc. Natl. Acad. Sci USA (2008) 42:16266-16271.

Fan, Quake SR (2010) "Sensitivity of Noninvasive Prenatal Detection of Fetal Aneuploidy from Maternal Plasma Using Shotgun Sequencing is Limited Only by Counting Statistics," PLoS ONE 5(5).

Harris et al., "Single-Molecule DNA Sequencing of a Viral Genome," Science (2008) 320:106-109.

Kagan et al. "Screening for Trisomies 21, 18 and 13 by Maternal Age, Fetal Nuchal Translucency, Fetal Heart Rate, Free b-hCG and Pregnancy-Associated Plasma Protein-A, " Human Reproduction (2008) 23(9):1968-1975.

Lo et al., "Presence of Fetal DNA in Maternal Plasma and Serum," Lancet (1997) 350:485-487.

Lo et al.,"Quantitative Analysis of Fetal DNA in Maternal Plasma and Serum: Implications for Noninvasive Prenatal Diagnosis," Am. J. Hum. Genet. (1998) 62:768-775.

Malone et al, "First-Trimester or Second-Trimester Screening, or Both, for Down's Syndrome," N. Engl. J. Med. (2005) 353:2001-2011.

Margulies et al., "Genome Sequencing in Microfabricated High-Density Picolitre Reactors," Nature (2005) 437:376-380.

Mewar et al., "Clinical and Molecular Evaluation of Four Patients with Partial Duplications of the Long Arm of Chromosome 18," Am J. Hum. Genet. (1993) 53(6):1269-1278.

Ostler, (2004) "Diseases of the Eye and Skin: A Color Atlas," Lippincott Williams & Wilkins. p. 72, ISBN 9780781749992.

Pertl et al., "Fetal DNA in Maternal Plasma: Emerging Clinical Applications," Obstetrics and Gynecology (2001) 98:483-490.

Rogers et al., "Genomics: Massively Parallel Sequencing," Nature (2005) 437:326-327.

Soni et al.,"Progress Toward Ultrafast DNA Sequencing Using Solid-State Nanopores," Clin. Chem. (2007) 53(11):1996-2001.

Sybert et al., "Turner's Syndrome," N. Engl. J. Med. (2004) 351:1227-1238.

Agresti, "Logistic Regression," Categorical Data Analysis, 2nd Edition, John Wiley & Sons, Inc. (2002) Ch. 5, pp. 165, 183, 184.

Chiu et al., "Maternal Plasma DNA Analysis with Massively Parallel Sequencing by Ligation for Noninvasive Prenatal Diagnosis of Trisomy 21," Clinical Chemistry (2010) 56(3):459-463.

Communication pursuant to Article 94(3) EPC for EP 11 863 253.8, mailed Jul. 24, 2013, 8 pages.

Communication pursuant to Article 94(3) EPC for EP 11 863 253.8, mailed Feb. 24, 2014, 5 pages.

Office Action (with translation) for CN 201180067286.X, mailed Apr. 3, 2014, 12 pages.

Response (with translation) to Office Action 1, dated Apr. 3, 2014, for CN 201180067286.X, 7 pages.

Office Action for CA 2,791,118, mailed Apr. 7, 2014, 17 pages.

Patent Examination Report No. 1 for AU 2012261664, mailed Apr. 7, 2014, 2 pages.

Response to Communication pursuant to Article 94(3) EPC, filed Apr. 28, 2014, 57 pages.

Substantive Examination Adverse Report for MY PI 2012005470, mailed Apr. 30, 2014, 3 pages.

Response to First Examination Report for AU 2012261664, filed Jun. 5, 2014, 15 pages.

"BGI performed more than one million NIFTY tests worldwide," BGI News (Mar. 25, 2016), http://www.genomics.cn/en/news/show_news?nid=104857.

Cheung et al., "Accurate description of DNA-Based noninvasive prenatal screening," N Engl J Med (2015) 372(17):1675-1677 (Including Supplementary Appendix pp. 1-4).

Zhang et al., "Non-invasive prenatal testing for trisomies 21, 18 and 13: clinical experience from 146 958 pregnancies," Ultrasound Obstet Gynecol (2015) 45:530-538.

* cited by examiner

METHOD FOR DETERMINING FETAL CHROMOSOMAL ABNORMALITY

CROSS-REFERENCE TO RELATED APPLICATIONS

This application is the national phase of PCT application PCT/CN2011/001070 having an international filing date of Jun. 29, 2011. The content of the above-listed PCT application is incorporated herein by this reference in its entirety.

TECHNICAL FIELD

The invention relates to noninvasive methods for the detection of fetal genetic abnormality by DNA sequencing of samples from pregnant women. More particularly, this invention relates to data analysis to remove GC bias introduced by amplification and sequencing of DNA samples. This invention further relates to statistical analysis to detect fetal genetic abnormalities, such as chromosomal abnormalities including aneuploidy.

BACKGROUND ART

Conventional prenatal diagnostic methods with invasive procedures, such as chorionic villus sampling and amniocentesis, carry potential risks for both fetuses and mothers. Noninvasive screening of fetal aneuploidy using maternal serum markers and ultrasound are available but have limited sensitivity and specificity (Kagan, et al., Human Reproduction (2008) 23:1968-1975; Malone, et al., N Engl J Med (2005) 353:2001-2011).

Recent studies have demonstrated noninvasive detection of fetal aneuploidy by massively parallel sequencing of DNA molecules in the plasma of pregnant women is feasible. Fetal DNA has been detected and quantitated in maternal plasma and serum (Lo, et al., Lancet (1997) 350:485 487; Lo, et al., Am. J. hum. Genet. (1998) 62:768-775). Multiple fetal cell types occur in the maternal circulation, including fetal granulocytes, lymphocytes, nucleated red blood cells, and trophoblast cells (Pertl and Bianchi, Obstetrics and Gynecology (2001) 98:483-490). Fetal DNA can be detected in the serum at the seventh week of gestation, and increases with the term of the pregnancy. The fetal DNA present in the maternal serum and plasma is comparable to the concentration of DNA obtained from fetal cell isolation protocols.

Circulating fetal DNA has been used to determine the sex of the fetus (Lo, et al., Am. J. hum. Genet. (1998) 62:768-775). Also, fetal rhesus D genotype has been detected using fetal DNA. However, the diagnostic and clinical applications of circulating fetal DNA is limited to genes that are present in the fetus but not in the mother (Pertl and Bianchi, Obstetrics and Gynecology (2001) 98:483-490). Thus, a need still exists for a non invasive method that can determine the sequence of fetal DNA and provide definitive diagnosis of chromosomal abnormalities in a fetus.

The discovery of fetal cells and cell-free fetal nucleic acids in maternal blood in the past few decades and the application of high-throughput shotgun sequencing of maternal plasma cell-free DNA make it is available to detect small changes in the representation of chromosomes contributed by an aneuploid fetus in a maternal plasma sample. Non-invasive detection of trisomy 13, 18, and 21 pregnancies have been achieved.

However, as some studies show, GC bias introduced by amplification and sequencing placed a practical limit on the sensitivity of aneuploidy detection. GC bias might be introduced during the sample preparation and the sequencing process, under different conditions such as reagent composition, cluster density and temperature, which leads to differential sampling of DNA molecules with different GC composition and significant variation in sequencing data for chromosomes that are GC-rich or GC-poor.

To improve sensitivity, protocols for removal of the effect of GC-bias have been developed. Fan and Quake developed a method to computationally remove GC bias by applying weight to each GC density based on local genomic GC content, to ameliorate the number of reads mapped in each bin by multiplying corresponding weight (Fan and Quake PLoS ONE (2010) 5:e10439). However, the method has difficulty in dealing with sex chromosome disorders especially chromosome Y relevant disorders for the reason that the process may cause slight distortion of data which will interfere with the precision of detection.

Here, we describe a method to computationally remove the GC-bias in order to get a higher sensitivity in fetal genetic abnormality detection as well as avoid data distortion. This method defines parameters used for statistical test according to GC-content. In addition, we introduced the estimated fetal fraction into the diagnosis by binary hypothesis which showed higher sensitivity and specificity. Our method also shows it should be possible to increase the sensitivity of noninvasive detection of fetal genetic abnormality to preset precision for maternal sample containing a low fetal DNA fraction by sequencing more polynucleotide fragments. Resampling of maternal plasma in later gestational weeks may also increase the sensitivity of diagnosis.

SUMMARY OF THE INVENTION

The current invention is directed to methods for noninvasive detection of fetal genetic abnormalities by large-scale sequencing of nucleotides from maternal biological sample. Further provided are methods to remove GC bias from the sequencing results because of the difference in GC content of a chromosome.

Therefore, in one aspect, provided herein is a method for establishing a relationship between coverage depth and GC content of a chromosome, which method comprises: obtaining sequence information of multiple polynucleotide fragments covering said chromosome and another chromosome from more than one sample; assigning said fragments to chromosomes based on said sequence information; calculating coverage depth and GC content of said chromosome based on said sequence information for each sample; and determining the relationship between the coverage depth and GC content of said chromosome.

In one embodiment the polynucleotide fragments range from about 10 to about 1000 bp in length. In another embodiment the polynucleotide fragments range from about 15 to about 500 bp in length. In yet another embodiment the polynucleotide fragments range from about 20 to about 200 bp in length. In still another embodiment the polynucleotide fragments range from about 25 to about 100 bp in length. In a further embodiment the polynucleotide fragments are about 35 bp in length.

In one embodiment, the sequence information is obtained by parallel genomic sequencing. In another embodiment the assignment of the fragment to chromosomes is by comparing the sequence of the fragments with a reference human genomic sequence. The reference human genomic sequence may be any suitable and/or published human genome builds, such as hg18 or hg19. The fragments that assign to more than one chromosome or do not assign to any chromosome may be disregarded.

In one embodiment the coverage depth of a chromosome is the ratio between the number of fragments that assigns to the chromosome and the number of reference unique reads of the chromosome. In another embodiment, the coverage depth is normalized. In still another embodiment, the normalization is calculated against the coverage of all other autosomes. In yet another embodiment, the normalization is calculated against the coverage of all other chromosomes.

In one embodiment, the relationship is in the formula:

$$cr_{i,j} = f(GC_{i,j}) + \epsilon_{i,j}, j=1,2,\ldots,22,X,Y$$

wherein $f(GC_{i,j})$ represents the function of the relationship between normalized coverage depth and the corresponding GC content of sample i, chromosome j, $\epsilon_{i,j}$ represents the residual of sample i, chromosome j. In some embodiments, the relationship between coverage depth and GC content is calculated by local polynomial regression. In some embodiments, the relationship may be a non-strong linear relationship. In some embodiments, the relationship is determined by loess algorithm.

In some embodiments, the method further comprises calculating fitted coverage depth according to the formula:

$$c\hat{r}_{i,j} = f(GC_{i,j}), j=1,2,\ldots,22,X,Y.$$

In some embodiments, the method further comprises calculating standard variation according to the formula:

$$std_j = \sqrt{\sum_i (cr_{i,j} - c\hat{r}_{i,j})^2/(ns-1)}, j=1,2,\ldots,22,X,Y,$$

wherein ns represents the number of reference samples.

In some embodiments, the method further comprises calculating student t-statistic according to the formula:

$$t1_{i,j} = (cr_{i,j} - c\hat{r}_{i,j})/std_j, j=1,2,\ldots,22,X,Y.$$

In one embodiment, the GC content of a chromosome is the average GC content of all fragments that assign to the chromosome. The GC content of a fragment may be calculated by dividing the number of G/C nucleotides in the fragment by the total number of nucleotides of the fragment. In another embodiment, the GC content of a chromosome is the aggregate GC content of the reference unique reads of the chromosome.

In some embodiments, at least 2, 5, 10, 20, 50, 100, 200, 500 or 1000 samples are used. In some embodiments, the chromosome is chromosome 1, 2, . . . , 22, X or Y.

In one embodiment, the samples are from pregnant female subjects. In another embodiment, the samples are from male subjects. In still another embodiment, the samples are from both pregnant female subjects and make subjects.

In some embodiments, the samples are biological samples. In some embodiments, the samples are peripheral blood samples.

Also provided herein is a method to determine a fetal genetic abnormality, which method comprises: a) obtaining sequence information of multiple polynucleotide fragments from a sample; b) assigning said fragments to chromosomes based on said sequence information; c) calculating coverage depth and GC content of a chromosome based on said sequence information; d) calculating fitted coverage depth of said chromosome using said GC content of said chromosome and an established relationship between coverage depth and GC content of said chromosome; and e) comparing said fitted coverage depth to said coverage depth of said chromosome, wherein a difference between them indicates fetal genetic abnormality.

In some embodiments, the method further comprises step f) determining the fetal gender. The fetal gender may be determined according to the formula:

$$logit(p_i) = \ln\left(\frac{p_i}{1-p_i}\right) = \beta_0 + \beta_1 cr \cdot a_{i,x} + \beta_2 cr \cdot a_{i,y},$$

wherein $cr \cdot a_{i,x}$ and $cr \cdot a_{i,y}$ are normalized relative coverage of X and Y chromosomes, respectively.

In some embodiments, the method further comprises step g) estimating the fetal fraction. The fetal fraction may be calculated according to the formula:

$$fy_i = (cr_{i,Y} - \hat{cr}_{i,Yf})/(\hat{cr}_{i,Ym} - \hat{cr}_{i,Yf}),$$

wherein $\hat{cr}_{i,Yf} = f(GC_{i,Yf})$ is the fitted coverage depth calculated from the relationship of the chromosome Y coverage depth and corresponding GC content of samples from pregnant women with a female fetus, $\hat{cr}_{i,Ym} = f(GC_{i,Ym})$ refers to the fitted coverage depth calculated from the relationship of the chromosome Y coverage depth and corresponding GC content of samples from male subjects. Alternatively, the fetal fraction may be calculated according to the formula:

$$fx_i = (cr_{i,x} - \hat{cr}_{i,Xf})/(\hat{cr}_{i,Xm} - \hat{cr}_{i,Xf}),$$

wherein $\hat{cr}_{i,Xf} = f(GC_{i,Xf})$ is the fitted coverage depth calculated from the relationship of the chromosome X coverage depth and corresponding GC content of samples from pregnant women with a female fetus, $\hat{cr}_{i,Ym} = f(GC_{i,Ym})$ refers to the fitted coverage depth calculated from the relationship of the chromosome X coverage depth and corresponding GC content of samples from male subjects. Further, the fetal fraction may be calculated according to the formula:

$$fxy_i = \arg\min_{\varepsilon \in (0,1)} \left( \frac{(\hat{cr}_{i,Xf} \cdot (1-\varepsilon) + \hat{cr}_{i,Xm} \cdot \varepsilon - cr_{i,X})^2}{(\hat{\sigma}_{X,f} \cdot (1-\varepsilon))^2 + (\hat{\sigma}_{X,m} \cdot \varepsilon)^2} + \frac{(\hat{cr}_{i,Yf} \cdot (1-\varepsilon) + \hat{cr}_{i,Ym} \cdot \varepsilon - cr_{i,X})^2}{(\hat{\sigma}_{Y,f} \cdot (1-\varepsilon))^2 + (\hat{\sigma}_{Y,m} \cdot \varepsilon)^2} \right),$$

wherein $\hat{cr}_{i,Xf} = f(GC_{i,Xf})$ is the fitted coverage depth calculated from the relationship of the chromosome X coverage depth and corresponding GC content of samples from pregnant women with a female fetus, $\hat{cr}_{i,Yf} = f(GC_{i,Yf})$ refers to the fitted coverage depth calculated from the relationship of the chromosome Y coverage depth and corresponding GC content of samples from pregnant women with a female fetus, $\hat{cr}_{i,Xm} = f(GC_{i,Xm})$ refers to the fitted coverage depth calculated from the relationship of the chromosome X coverage depth and corresponding GC content of samples from male subjects, $\hat{cr}_{i,Ym} = f(GC_{i,Ym})$ refers to the fitted coverage depth calculated from the relationship of the chromosome Y coverage depth and corresponding GC content of male subjects.

In one embodiment, the genetic abnormality is a chromosomal abnormality. In another embodiment, the genetic abnormality is aneuploidy. In still another embodiment, the fetal aneuploidy is a disorder for an autosome selected from the group consisting of trisomy 13, 18 and 21. In yet another embodiment, the fetal aneuploidy is a disorder for a sex chromosome selected from the group consisting of XO, XXX, XXY and XYY.

In some embodiments, the comparison of said fitted coverage depth to said coverage depth of the chromosome is conducted by a statistical hypothesis test, wherein one hypothesis is that the fetus is euploid (H0) and the other hypothesis is that the fetus is aneuploid (H1). A statistic may be calculated for both hypotheses. In some embodiments, the student t-statistic is calculated for H0 and H1 according to formula: $t1_{i,j}=(cr_{i,j}-c\hat{r}_{i,j})/std_j$ and $t2_{i,j}=(cr_{i,j}-c\hat{r}_{i,j}(1+fxy_{i,j}/2)))/std_j$, respectively, wherein fxy is fetal fraction. In some embodiments, the log likelihood ratio of t1 and t2 is calculated according to formula: $L_{i,j}=\log(p(t1_{i,j}, \text{degree}|D))/\log(p(t2_{i,j}, \text{degree}|T))$, wherein degree refers to at distribution degree, D refers to Diploidy, T refers to Trisomy, and $p(t1_{i,j},\text{degree}|*),*=D,T$ represents conditional probability density given at distribution degree.

In one embodiment, the fetal gender is female, and the student t-statistic is calculated according to formula: $t1_{i,x}=(cr_{i,x}-c\hat{r}_{i,xf})/std_{xf}$, wherein $c\hat{r}_{i,xf}=f(GC_{i,xf})$ is the fitted coverage depth calculated from the relationship of the chromosome X coverage depth and corresponding GC content of samples from pregnant women with a female fetus. In some embodiments, $|t1|>3.13$ indicates the fetus may be XXX or XO. In some embodiments, $|t1|>5$ indicates the fetus is XXX or XO.

In another embodiment, the fetal gender is male, and the student t-statistic is calculated according to formula: $t2_i=(cr_{i,x}-(1-fy_i/2)\cdot c\hat{r}_{i,xf})/std_{xf}$, wherein $c\hat{r}_{i,xf}=f(GC_{i,xf})$ is the fitted coverage depth calculated from the relationship of the chromosome X coverage depth and corresponding GC content of samples from pregnant women with a female fetus. In some embodiments, $|t2|>3.13$ indicates the fetus may be XXY or XYY. In some embodiments, $|t2|>5$ indicates the fetus is XXY or XYY.

Further provided herein is a method to determine a fetal genetic abnormality, which method comprises: a) obtaining sequence information of multiple polynucleotide fragments covering a chromosome and another chromosome from more than one normal samples; b) assigning said fragments to chromosomes based on said sequence information; c) calculating coverage depth and GC content of said chromosome based on said sequence information from said normal samples; d) determining the relationship between the coverage depth and GC content of said chromosome; e) obtaining sequence information of multiple polynucleotide fragments from a biological sample; f) assigning said fragments to chromosomes based on said sequence information from said biological sample; g) calculating coverage depth and GC content of said chromosome based on said sequence information from said biological sample; h) calculating fitted coverage depth of said chromosome using said GC content of said chromosome and said relationship between coverage depth and GC content of said chromosome; and i) comparing said fitted coverage depth to said coverage depth of said chromosome, wherein a difference between them indicates fetal genetic abnormality.

In another aspect, provided herein is a computer readable medium comprising a plurality of instructions for performing prenatal diagnosis of a fetal genetic abnormality, which comprises the steps of: a) receiving sequence information of multiple polynucleotide fragments from a sample; b) assigning said polynucleotide fragments to chromosomes based on said sequence information; c) calculating coverage depth and GC content of a chromosome based on said sequence information; d) calculating fitted coverage depth of said chromosome using said GC content of said chromosome and an established relationship between coverage depth and GC content of said chromosome; and e) comparing said fitted coverage depth to said coverage depth of said chromosome, wherein a difference between them indicates genetic abnormality.

In still another aspect, provided herein is a system for determining fetal genetic abnormality, which method comprises: a) means for obtaining sequence information of multiple polynucleotide fragments from a sample; and b) a computer readable medium comprising a plurality of instructions for performing prenatal diagnosis of a fetal genetic abnormality. In some embodiments, the system further comprises a biological sample obtained from a pregnant female subject, wherein the biological sample includes multiple polynucleotide fragments.

BRIEF DESCRIPTION OF THE DRAWINGS

FIG. 8 shows the histogram of chromosome Y coverage depth. There are two peaks which implicates that the gender of cases can be distinguished by the coverage depth of chromosome Y. The curve is distribution of relative coverage depth of chromosome Y estimated by kernel density estimation with Gaussian kernel.

FIG. 9 shows a diagram of the process for diagnosing 903 test samples for fetal chromosome abnormality.

FIG. 10 shows the result of aneuploidy: trisomy 13, 18, 21 and XO, XXY, XYY cases and normal cases. FIG. 10A shows the plots of normalized coverage depth vs. GC content of chromosomes 13, 18 and 21. FIG. 10B shows the plots of chromosomes X and Y. Circles represent normal female fetuses' relative coverage dept with GC content, dots represent normal male fetuses. The solid line is fitting line of relative coverage and GC content, the dash lines are t-value absolute is 1, the dotted lines are absolute of t-value is 2 and the dotdash lines: absolute of t-value is 3.

FIG. 11 compares the confidence value of different diagnostic approaches.

FIG. 12 shows the relationship between fetal DNA fraction and gestational age. The fraction of fetal DNA in maternal plasma correlates with gestational age. Fetal DNA fraction was estimated by X and Y together. There is a statistically significant correlation between the average fetal DNA fraction and gestational age (P<0.001). Note that the R2 value represents the square of the correlation coefficient is small. The minimum fraction is 3.49%.

FIG. 13 shows the relationship between the standard variance with the case number required for detection. The standard variances computed by Formula 5 of every chromosome vary with different number of samples. The standard variance becomes stable when the number of samples is larger than 100.

FIG. 14 shows the estimated number of unique reads for the detection of fetal aneuploidy in cell-free plasma as a function of fetal DNA fraction. The estimates are based on level of confidence t-value no smaller than 3 for aneuploidy of chromosomes 13, 18, 21, and X, even Y (from the relationship between X and Y) each having different length. As fetal DNA fraction decreases, the total number of shotgun sequences required increases. With a sequencing throughput of 4 million sequence reads per channel on the flowcell, trisomy 21 can be detected if 3.5% of the cell-free DNA is fetal. Aneuploidy of chromosome X was not detected easily when the fraction and unique reads number are small, such as 4% and 5 million reads. Different chromosome requires different level of fetal DNA fraction and unique reads number, which may be caused by the GC structure of the chromosome.

FIG. 15 shows a contour graph of sensitivity mapped by data volume and gestational age (weeks) for detection of trisomy of chromosome 13 for female fetuses, for every gestational week and every point of data volume.

FIG. 16 shows a contour graph of sensitivity mapped by data volume and gestational age (weeks) for detection of trisomy of chromosome 18 for female fetuses, for every gestational week and every point of data volume.

FIG. 17 shows a contour graph of sensitivity mapped by data volume and gestational age (weeks) for detection of trisomy of chromosome 21 for female fetuses, for every gestational week and every point of data volume.

FIG. 18 shows a contour graph of sensitivity mapped by data volume and gestational age (weeks) for detection of trisomy of chromosome X for female fetuses, for every gestational week and every point of data volume.

FIG. 19 shows a contour graph of sensitivity mapped by data volume and gestational age (weeks) for detection of trisomy of chromosome 13 of male. For every gestational week and every point of data volume, we compute its empirical distribution of fetal DNA fraction and standard variance for given data volume firstly, and comparing the fraction estimated by XY or Y then we compute the sensitivity of every type of aneuploidy.

FIG. 20 shows a contour graph of sensitivity mapped by data volume and gestational age (weeks) for detection of trisomy of chromosome 18 of male.

FIG. 21 shows a contour graph of sensitivity mapped by data volume and gestational age (weeks) for detection of trisomy of chromosome 21 of male.

DETAILED DESCRIPTION OF THE INVENTION

Figure 1:
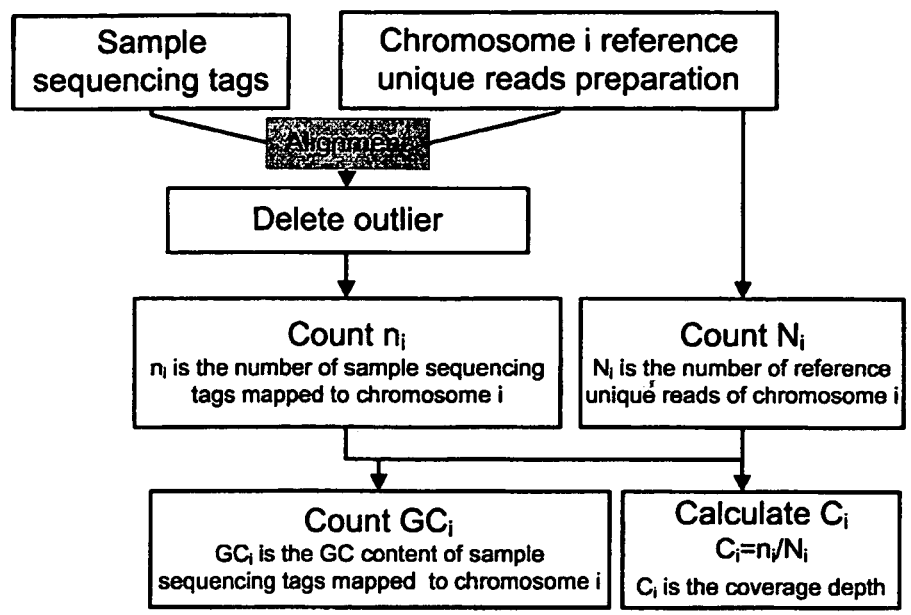
FIG. 1 shows a schematic process for calculating the coverage depth and GC content by using sequence information of polynucleotide fragments.
Figure 2A:
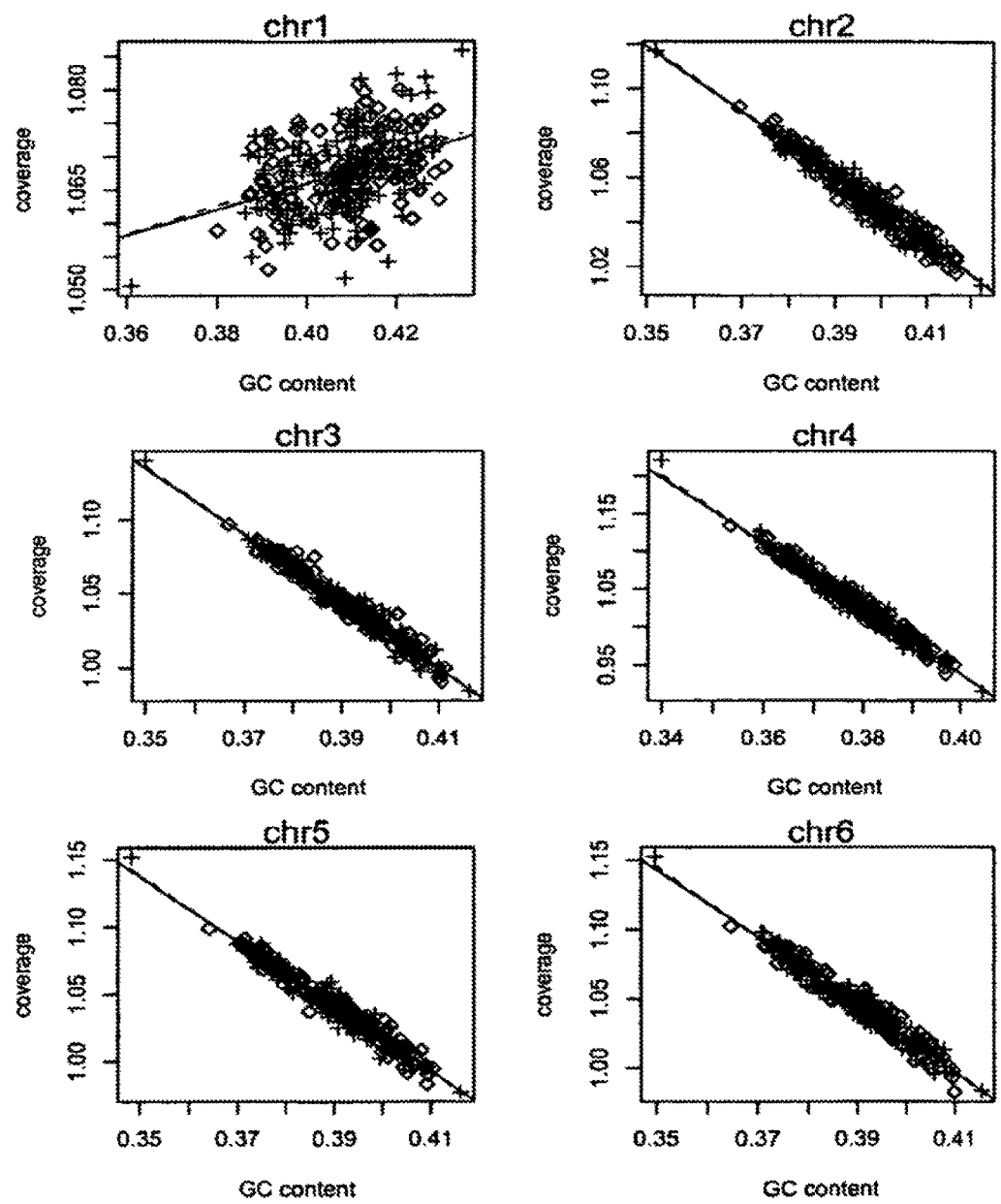
FIGS. 2A-D illustrate the normalized coverage depth-GC content correlation establishing by using data from 300 reference cases. The normalized coverage depth for each case is plotted against corresponding sequenced GC content. Crosses denote cases with euploid female fetus, squares denote cases with euploid male fetus. The solid line is the fitting line of the coverage depth and GC content.
Figure 2B:
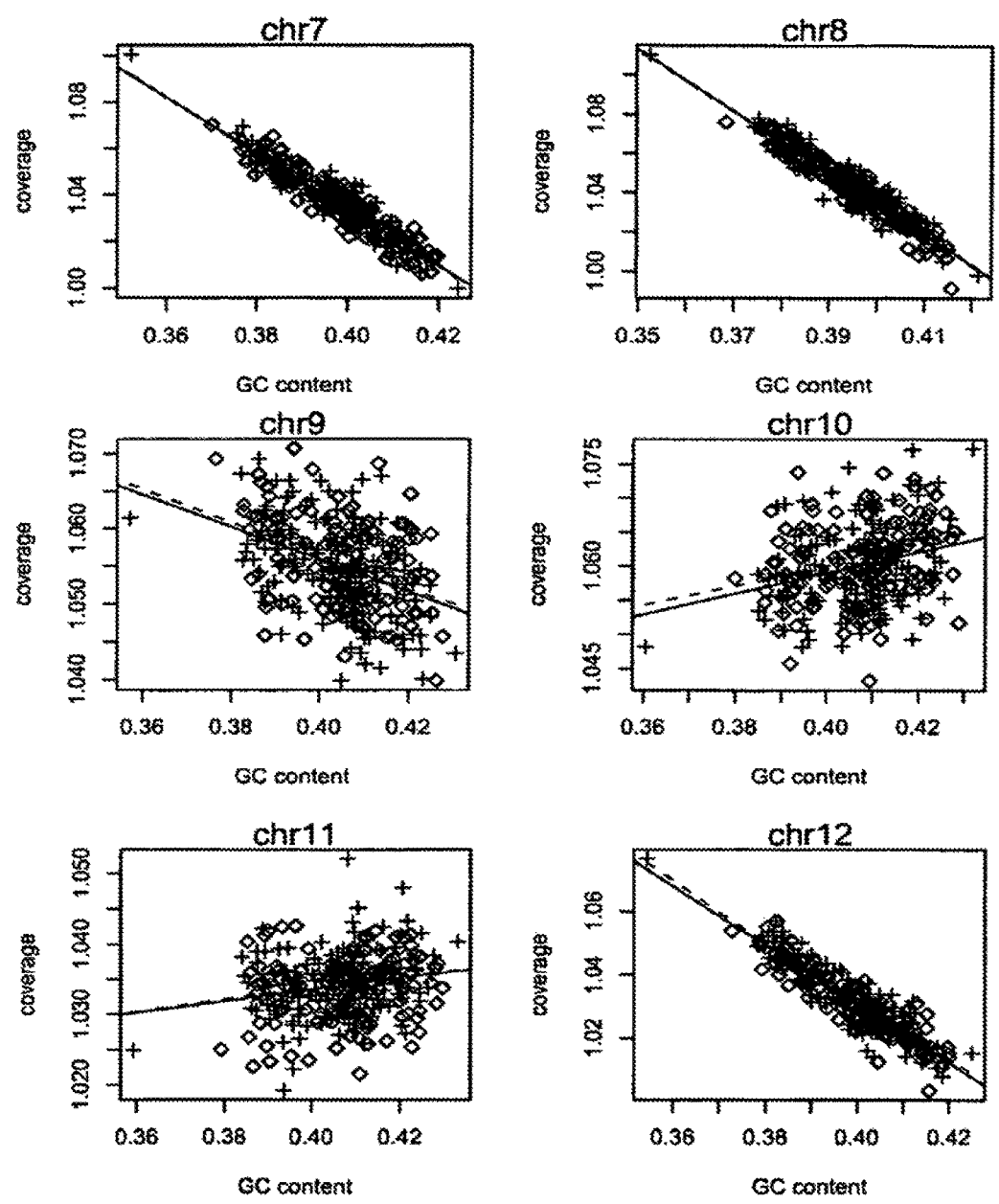
Figure 2C:
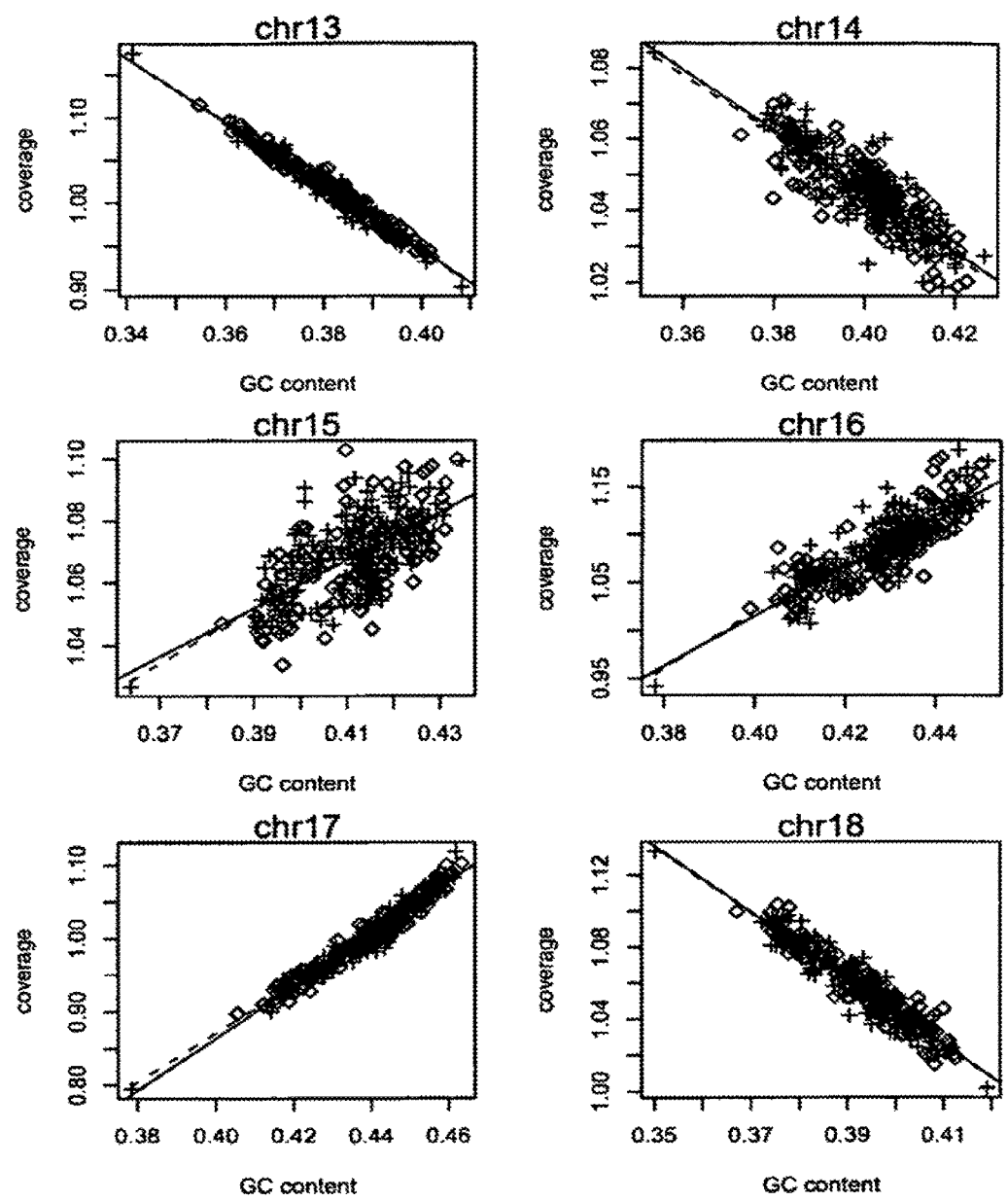
Figure 2D:
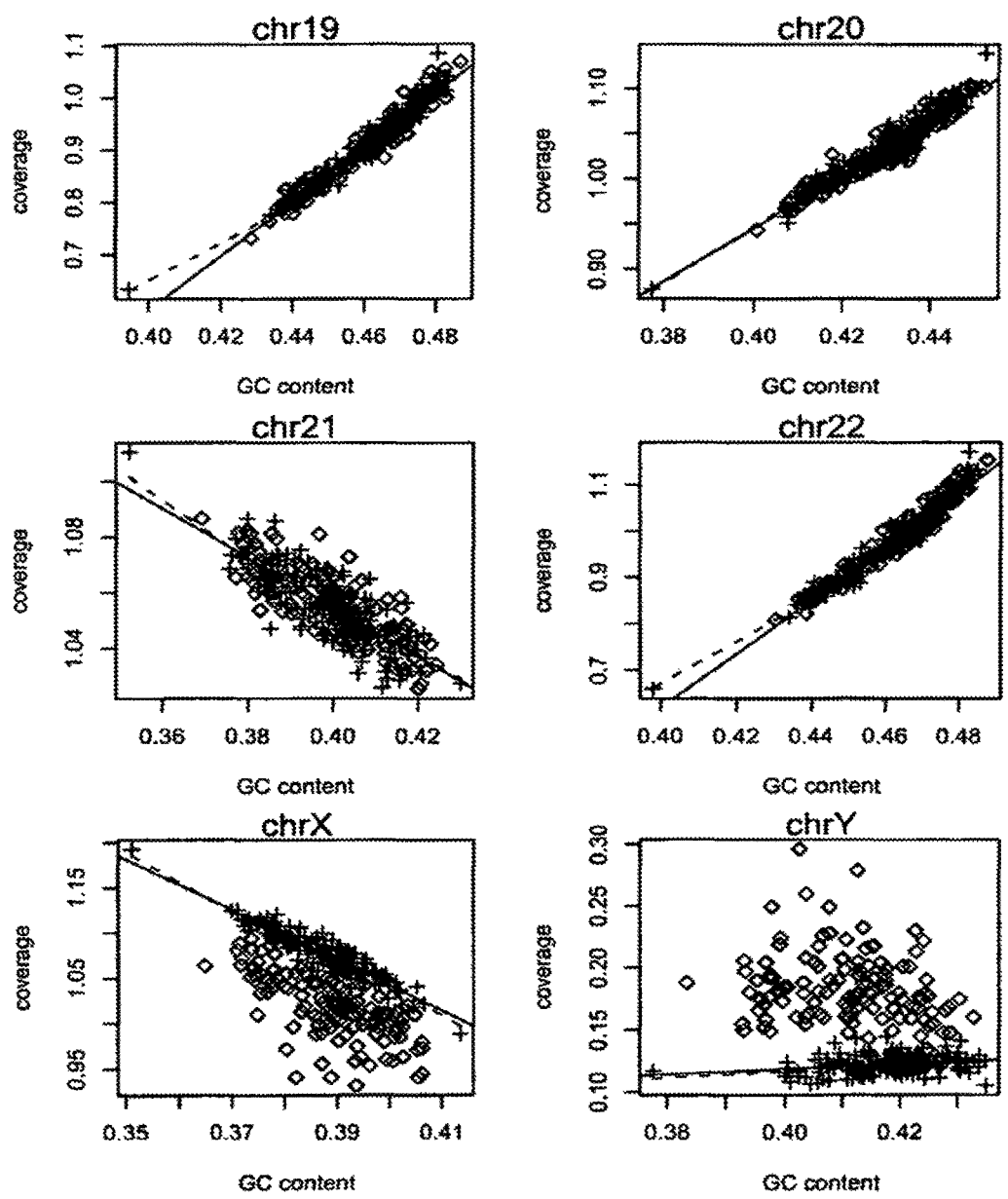

The current invention is directed to methods for noninvasive detection of fetal genetic abnormalities by large-scale sequencing of polynucleotide fragments from a maternal biological sample. Further provided are methods to remove GC bias from the sequencing results because of the difference in GC content of a chromosome based on the relationship between the coverage depth of a chromosome and the corresponding GC content. Accordingly, provided herein is a method to computationally adjust reference parameters being used in student-t calculation with GC contents by locally weighted polynomial regression to fit the coverage depth of a chromosome of each sample against the GC content of the polynucleotide fragments.

Also provided herein is a method of determining the genetic abnormality of a fetus by statistical analysis using a statistical hypothesis test. In addition, methods are provided to calculate data quality control (DQC) standards useful in determining the amount of clinical samples needed for a certain statistical significance level.

I. Definitions

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, the singular forms "a", "an", and "the" include plural references unless indicated otherwise. For example, "a" dimer includes one or more dimers.

The term "chromosomal abnormality" refers to a deviation between the structure of the subject chromosome and a normal homologous chromosome. The term "normal" refers to the predominate karyotype or banding pattern found in healthy individuals of a particular species. A chromosomal abnormality can be numerical or structural, and includes but is not limited to aneuploidy, polyploidy, inversion, a trisomy, a monosomy, duplication, deletion, deletion of a part of a chromosome, addition, addition of a part of chromosome, insertion, a fragment of a chromosome, a region of a chromosome, chromosomal rearrangement, and translocation. A chromosomal abnormality can be correlated with presence of a pathological condition or with a predisposition to develop a pathological condition. As defined herein, a single nucleotide polymorphism ("SNP") is not a chromosomal abnormality.

Monosomy X (XO, absence of an entire X chromosome) is the most common type of Turner syndrome, occurring in 1 in 2500 to 1 in 3000 live-born girls (Sybert and McCauley *N Engl J Med* (2004) 351:1227-1238). XXY syndrome is a condition in which human males have an extra X chromosome, existing in roughly 1 out of every 1000 males (Bock, *Understanding Klinefelter Syndrome: A Guide for XXY Males and Their Families*. NIH Pub. No. 93-3202 (1993)). XYY syndrome is an aneuploidy of the sex chromosomes in which a human male receives an extra Y chromosome, giving a total of 47 chromosomes instead of the more usual 46, affecting 1 in 1000 male births while potentially leading to male infertility (Aksglaede, et al., *J Clin Endocrinol Metab* (2008) 93:169-176).

Turner syndrome encompasses several conditions, of which monosomy X (XO, absence of an entire sex chromosome, the Barr body) is most common. Typical females have two X chromosomes, but in Turner syndrome, one of those sex chromosomes is missing. Occurring in 1 in 2000 to 1 in 5000 phenotypic females, the syndrome manifests' itself in a number of ways. Klinefelter syndrome is a condition in which human males have an extra X chromosome. In humans, Klinefelter syndrome is the most common sex chromosome disorder and the second most common condition caused by the presence of extra chromosomes. The condition exists in roughly 1 out of every 1,000 males. XYY syndrome is an aneuploidy of the sex chromosomes in which a human male receives an extra Y chromosome, giving a total of 47 chromosomes instead of the more usual 46. This produces a 47, XYY karyotype. This condition is usually asymptomatic and affects 1 in 1000 male births while potentially leading to male infertility.

Trisomy 13 (Patau syndrome), trisomy 18 (Edward syndrome) and trisomy 21 (Down syndrome) are the most clinically important autosomal trisomies and how to detect them has always been the hot topic. Detection of above fetal chromosomal aberration has great significance in prenatal diagnosis (Ostler, *Diseases of the eye and skin: a color atlas*. Lippincott Williams & Wilkins. pp. 72. ISBN 9780781749992 (2004); Driscoll and Gross *N Engl J Med* (2009) 360: 2556-2562; Kagan, et al., *Human Reproduction* (2008) 23:1968-1975).

The term "reference unique reads" refers to fragments of a chromosome that have a unique sequence. Therefore, such fragments can be unambiguously assigned to a single chromosomal location. Reference unique reads of a chromosome may be constructed based on a published reference genome sequence, such as hg18 or hg19.

The terms "polynucleotide," "oligonucleotide," "nucleic acid" and "nucleic acid molecule" are used interchangeably herein to refer to a polymeric form of nucleotides of any length, and may comprise ribonucleotides, deoxyribonucleotides, analogs thereof, or mixtures thereof. This term refers only to the primary structure of the molecule. Thus, the term includes triple-, double- and single-stranded deoxyribonucleic acid ("DNA"), as well as triple-, double- and single-stranded ribonucleic acid ("RNA"). It also includes modified, for example by alkylation, and/or by capping, and unmodified forms of the polynucleotide. More particularly, the terms "polynucleotide," "oligonucleotide," "nucleic acid" and "nucleic acid molecule" include polydeoxyribonucleotides (containing 2-deoxy-D-ribose), polyribonucleotides (containing D-ribose), including tRNA, rRNA, hRNA, and mRNA, whether spliced or unspliced, any other type of polynucleotide which is an N- or C-glycoside of a purine or pyrimidine base, and other polymers containing normucleotidic backbones, for example, polyamide (e.g., peptide nucleic acids ("PNAs")) and polymorpholino (commercially available from the Anti-Virals, Inc., Corvallis, Oreg., as NeuGene®) polymers, and other synthetic sequence-specific nucleic acid polymers providing that the polymers contain nucleobases in a configuration which allows for base pairing and base stacking, such as is found in DNA and RNA. Thus, these terms include, for example, 3'-deoxy-2',5'-DNA, oligodeoxyribonucleotide N3' to P5' phosphoramidates, 2'-O-alkyl-substituted RNA, hybrids between DNA and RNA or between PNAs and DNA or RNA, and also include known types of modifications, for example, labels, alkylation, "caps," substitution of one or more of the nucleotides with an analog, internucleotide modifications such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., aminoalkylphosphoramidates, aminoalkylphosphotriesters), those containing pendant moieties, such as, for example, proteins (including enzymes (e.g., nucleases), toxins, antibodies, signal peptides, poly-L-lysine, etc.), those with intercalators (e.g., acridine, psoralen, etc.), those containing chelates (of, e.g., metals, radioactive metals, boron, oxidative metals, etc.), those containing alkylators, those with modified linkages (e.g., alpha anomeric nucleic acids, etc.), as well as unmodified forms of the polynucleotide or oligonucleotide.

"Massively parallel sequencing" means techniques for sequencing millions of fragments of nucleic acids, e.g., using attachment of randomly fragmented genomic DNA to a planar, optically transparent surface and solid phase amplification to create a high density sequencing flow cell with millions of clusters, each containing ~1,000 copies of template per sq. cm. These templates are sequenced using four-color DNA sequencing-by-synthesis technology. See products offered by Illumina, Inc., San Diego, Calif. The presently used sequencing is preferably carried out without a preamplification or cloning step, but may be combined with amplification-based methods in a microfluidic chip having reaction chambers for both PCR and microscopic template-based sequencing. Only about 30 bp of random sequence information are needed to identify a sequence as belonging to a specific human chromosome. Longer sequences can uniquely identify more particular targets. In the present case, a large number of 35 bp reads were obtained. Further description of a massively parallel sequencing method is found in Rogers and Ventner, *Nature* (2005) 437:326-327.

As used herein, "biological sample" refers to any sample obtained from a living or viral source or other source of macromolecules and biomolecules, and includes any cell type or tissue of a subject from which nucleic acid or protein or other macromolecule can be obtained. The biological sample can be a sample obtained directly from a biological source or a sample that is processed. For example, isolated nucleic acids that are amplified constitute a biological sample. Biological samples include, but are not limited to, body fluids, such as blood, plasma, serum, cerebrospinal fluid, synovial fluid, urine and sweat, tissue and organ samples from animals and plants and processed samples derived therefrom.

It is understood that aspects and embodiments of the invention described herein include "consisting" and/or "consisting essentially of" aspects and embodiments.

Other objects, advantages and features of the present invention will become apparent from the following specification taken in conjunction with the accompanying drawings.

II. Establishing A Relationship between Coverage Depth and GC Content

Provided herein is a method for establishing a relationship between coverage depth and GC content of a chromosome, which method comprises: obtaining sequence information of multiple polynucleotide fragments covering said chromosome and another chromosome from more than one sample; assigning said fragments to chromosomes based on said sequence information; calculating coverage depth and GC content of said chromosome based on said sequence information for each sample; and determining the relationship between the coverage depth and GC content of said chromosome. The steps of operation may be carried out in no specific order. In some embodiments, the method may be carried out in the following order: a) obtaining sequence information of multiple polynucleotide fragments covering said chromosome and another chromosome from more than one sample; b) assigning said fragments to chromosomes based on said sequence information; c) calculating coverage depth and GC content of said chromosome based on said sequence information for each sample; and d) determining the relationship between the coverage depth and GC content of said chromosome.

To calculate the coverage depth and GC content of a chromosome location, sequence information of polynucleotide fragments is obtained by sequencing template DNA obtained from a sample. In one embodiment, the template DNA contains both maternal DNA and fetal DNA. In another embodiment, template DNA is obtained from blood of a pregnant female. Blood may be collected using any standard technique for blood drawing including but not limited to venipuncture. For example, blood can be drawn from a vein from the inside of the elbow or the back of the hand. Blood samples can be collected from a pregnant female at any time during fetal gestation. For example, blood samples can be collected from human females at 1-4, 4-8, 8-12, 12-16, 16-20, 20-24, 24-28, 28-32, 32-36, 36-40, or 40-44 weeks of fetal gestation, and preferably between 8-28 weeks of fetal gestation.

The polynucleotide fragments are assigned to a chromosome location based on the sequence information. A reference genomic sequence is used to obtain the reference unique reads. As used therein, the term "reference unique reads" refers to all the unique polynucleotide fragments that have been assigned to a specific genomic location based on a reference genomic sequence. In some embodiments, the reference unique reads have the same length of, for example, about 10, 12, 15, 20, 25, 30, 35, 40, 50, 100, 200, 300, 500, or 1000 bp. In some other embodiments, human genome builds hg18 or hg 19 may be used as the reference genomic sequence. A chromosome location may be a contiguous window on a chromosome that has a length of about 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10,000 or more KB. A chromosome location may also be a single chromosome.

As used herein, the term "coverage depth" refers to the ratio between the number of fragments that assigns to a chromosome location and the number of reference unique reads of the chromosome location using the following formula:

$$C_{i,j} = n_{i,j}/N_i, j=1,2,\ldots,22,X,Y \quad (1)$$

wherein $n_{i,j}$ is number of unique sequence reads mapped to chromosome j in sample i; $C_{i,j}$ is the coverage depth in chromosome j in sample i; $N_j$ is number of Reference Unique Reads in chromosome j.

In some embodiments, polynucleotide fragments that do not assign to a single chromosome location or assign to multiple chromosome locations are discarded. In some embodiments, the coverage depth is normalized, based on the coverage depth of another chromosome location, another chromosome, average of all other autosomes, average of all other chromosomes, or average of all chromosomes. In some embodiments, the average coverage depth of 22 autosomes is used as a normalization constant to account for the differences in total number of sequence reads obtained for different samples:

$$cr_{i,j} = C_{i,j} / \left( \sum_{j=1}^{22} C_{i,j}/22 \right), \quad (2)$$
$$j = 1, 2, \ldots, 22, X, Y$$

wherein $cr_{i,j}$ represents the relative coverage depth of chromosome j in sample i. From this point forward, "relative coverage depth" for each chromosome refers to the normalized value and is used for comparing different samples and for subsequent analysis.

GC content of a chromosome location can be calculated by the average GC percentage of a chromosome location based on the unique reference reads in the chromosome location, or on the sequenced polynucleotide fragments that assign to the chromosome location. GC content of a chromosome may be calculated using the following formula:

$$GC_{i,j} = NGC_{i,j}/BASE_{i,j} GC_{i,chrj} = \frac{no.GC_i}{no.BASE_i} \quad (3)$$

wherein i represents sample i, j represent chromosome j, $NGC_{i,j}$ represents the number of G and C DNA bases and $BASE_{i,j}$ represents the number of DNA bases on chromosome j in sample i.

The coverage depth and GC content may be based on the sequence information of polynucleotide fragments obtained from a single sample, or from multiple samples. To establish a relationship between the coverage depth and GC content of a chromosome location, the calculation may be based on the sequence information of polynucleotide fragments obtained from at least 1, 2, 5, 10, 20, 50, 100, 200, 500 or 1000 samples.

In some embodiments, the relationship between coverage depth and GC content is a non-strong linear relationship. Loess algorithm, or locally weighted polynomial regression, may be used to assess non-linear relationships (correlations) between pairs of values, such as between coverage depth and GC content.

III. Determining A Fetal Genetic Abnormality

Also provided herein is a method to determine a fetal genetic abnormality, which method comprises: a) obtaining sequence information of multiple polynucleotide fragments from a sample; b) assigning said fragments to chromosomes based on said sequence information; c) calculating coverage depth and GC content of a chromosome based on said sequence information; d) calculating fitted coverage depth of said chromosome using said GC content of said chromosome and an established relationship between coverage depth and GC content of said chromosome; and e) comparing said fitted coverage depth to said coverage depth of said chromosome, wherein a difference between them indicates fetal genetic abnormality.

The methods can be used to detect fetal chromosomal abnormalities, and is especially useful for the detection of aneuploidy, polyploidy, monosomy, trisomy, trisomy 21, trisomy 13, trisomy 14, trisomy 15, trisomy 16, trisomy 18, trisomy 22, triploidy, tetraploidy, and sex chromosome abnormalities including XO, XXY, XYY, and XXX. One may also focus on certain regions within the human genome according to the present methods in order to identify partial monosomies and partial trisomies. For example, the methods may involve analyzing sequence data in a defined chromosomal sliding "window," such as contiguous, nonoverlapping 50 Kb regions spread across a chromosome. Partial trisomies of 13q, 8p (8p23.1), 7q, distal 6p, 5p, 3q (3q25.1), 2q, 1q (1q42.1 and 1q21-qter), partial Xpand monosomy 4q35.1 have been reported, among others. For example, partial duplications of the long arm of chromosome 18 can result in Edwards syndrome in the case of a duplication of 18q21.1-qter (Mewar, et al., *Am J Hum Genet.* (1993) 53:1269-78).

In some embodiments, the fetal fraction is estimated based on the sequence information obtained for the polynucleotide fragments from a sample. The coverage depth, and GC content, of chromosome X and Y may be used for estimating the fetal fraction. In some embodiments, the fetal gender is determined based on the sequence information obtained for the polynucleotide fragments from a sample. The coverage depth, and GC content, of chromosome X and Y may be used for determining the fetal gender.

In some embodiments, the comparison of said fitted coverage depth to said coverage depth of the chromosome is conducted by a statistical hypothesis test, wherein one hypothesis is that the fetus is euploid (H0) and the other hypothesis is that the fetus is aneuploid (H1). In some embodiments, the student t-statistic is calculated for both hypotheses as t1 and t2, respectively. In some embodiments, the log likelihood ratio of t1 and t2 is calculated. In some embodiments, a log likelihood ratio of >1 indicates trisomy of the fetus.

IV. Computer Readable Medium and System for Diagnosis of A Fetal Genetic Abnormality In another aspect, provided herein is a computer readable medium comprising a plurality of instructions for performing prenatal diagnosis of a fetal genetic abnormality, which comprises the steps of: a) receiving said sequence information; b) assigning said polynucleotide fragments to chromosomes based on said sequence information; c) calculating coverage depth and GC content of said chromosome based on said sequence information; d) calculating fitted coverage depth of said chromosome using said GC content of said chromosome and an established relationship between coverage depth and GC content of said chromosome; and e) comparing said fitted coverage depth to said coverage depth of said chromosome, wherein a difference between them indicates genetic abnormality.

In still another aspect, provided herein is a system for determining fetal aneuploidy, which method comprises: a) means for obtaining sequence information from said polynucleotide fragments; and b) a computer readable medium comprising a plurality of instructions for performing prenatal diagnosis of a fetal genetic abnormality. In some embodiments, the system further comprises a biological sample obtained from a pregnant female subject, wherein the biological sample includes multiple polynucleotide fragments.

It will be apparent to those skilled in the art that a number of different sequencing methods and variations can be used. In one embodiment, the sequencing is done using massively parallel sequencing. Massively parallel sequencing, such as that achievable on the 454 platform (Roche) (Margulies, et al., *Nature* (2005) 437:376-380), Illumina Genome Analyzer (or Solexa™ platform) or SOLID System (Applied Biosystems) or the Helicos True Single Molecule DNA sequencing technology (Harris, et al., *Science* (2008) 320:106-109), the single molecule, real-time (SMRT™) technology of Pacific Biosciences, and nanopore sequencing (Soni and Meller, *Clin Chem* (2007) 53:1996-2001), allow the sequencing of many nucleic acid molecules isolated from a specimen at high orders of multiplexing in a parallel fashion (Dear, *Brief Funct Genomic Proteomic* (2003) 1:397-416). Each of these platforms sequences clonally expanded or even non-amplified single molecules of nucleic acid fragments. Commercially available sequencing equipment may be used in obtaining the sequence information of the polynucleotide fragments.

V. EXAMPLES

The following examples are offered to illustrate but not to limit the invention.

Example 1

Analysis of Factors that Affect Sensitivity of Detection: GC-Bias and Gender A schematic procedural framework for calculating coverage depth and GC content is illustrated in FIG. 1. We used software to produce the reference unique reads by incising the hg18 reference sequences into 1-mer (1-mer here is a read being artificially decomposed from the human sequence reference with the same "1" length with sample sequencing reads) and collected those "unique" 1-mer as our reference unique reads. Secondly, we mapped our sequenced sample reads to the reference unique reads of each chromosome. Thirdly, we deleted the outlier by applying quintile outlier cutoff method to get a clear data set. Finally, we counted the coverage depth of each chromosome for every sample and the GC content of the sequenced unique reads mapped to each chromosome for every sample.

Figure 3:
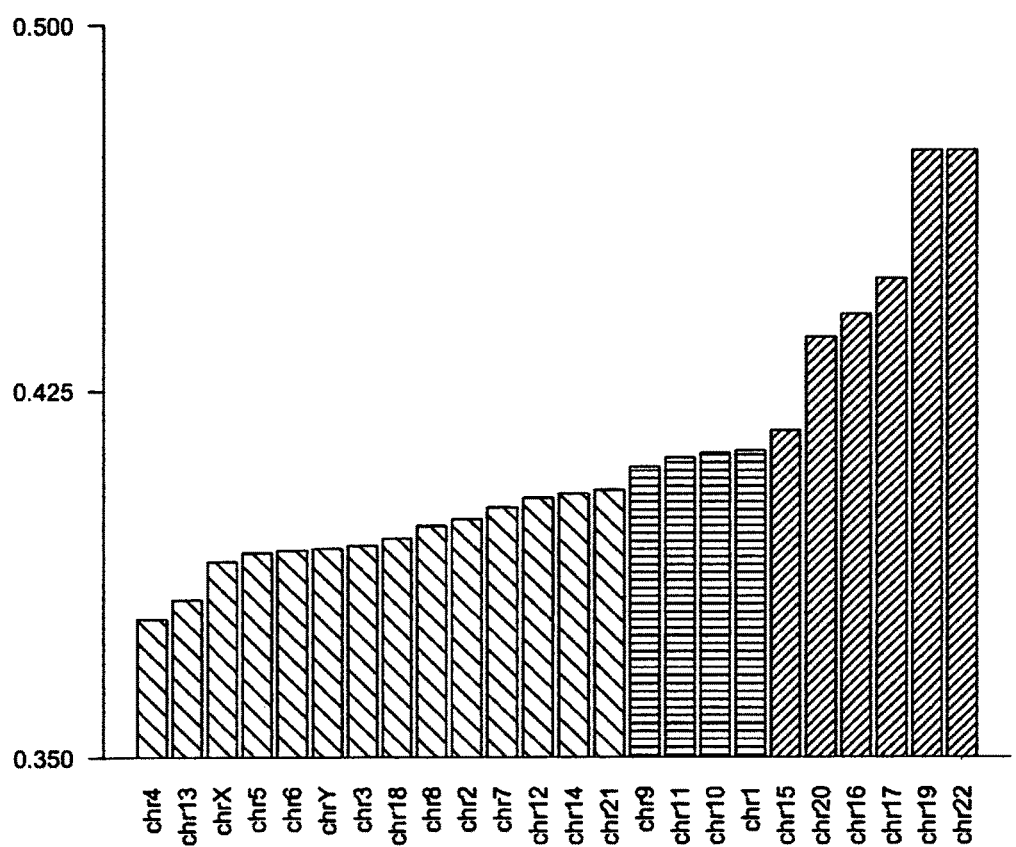
FIG. 3 illustrates the tendency between normalized coverage depth and corresponding GC content by arranging chromosomes with their inherent ascending GC content. The inherent ascending GC content of each chromosome here refers to the average GC content of sequenced tags of that chromosome from 300 reference cases.

In order to investigate how GC content affects our data, we chose 300 euploid cases with karyotype result and scattered their coverage depth and related GC content of sequenced reads into a graph, which showed a strong correlation between them, and this phenomenon was unreported previously (FIG. 2). In FIG. 2, coverage depth correlated strongly with the GC-content, and showed an obviously downward trend in some chromosomes such as 4, 13, etc., while upward trend in other chromosomes such as 19, 22, etc. All chromosomes were arranged in ascending order by their inherent GC-content and a downward tendency is present in lower GC-content group chromosomes while upward tendency in higher GC-content group chromosomes as shown in FIG. 3. It can be interpreted that if the polynucleotide fragments being sequenced for one sample has a higher GC-content than the other sample, the coverage depth representing this sample would drop comparing to that of the other sample in lower GC-content group chromosomes while rose in higher GC-content group chromosomes.

Figure 4:
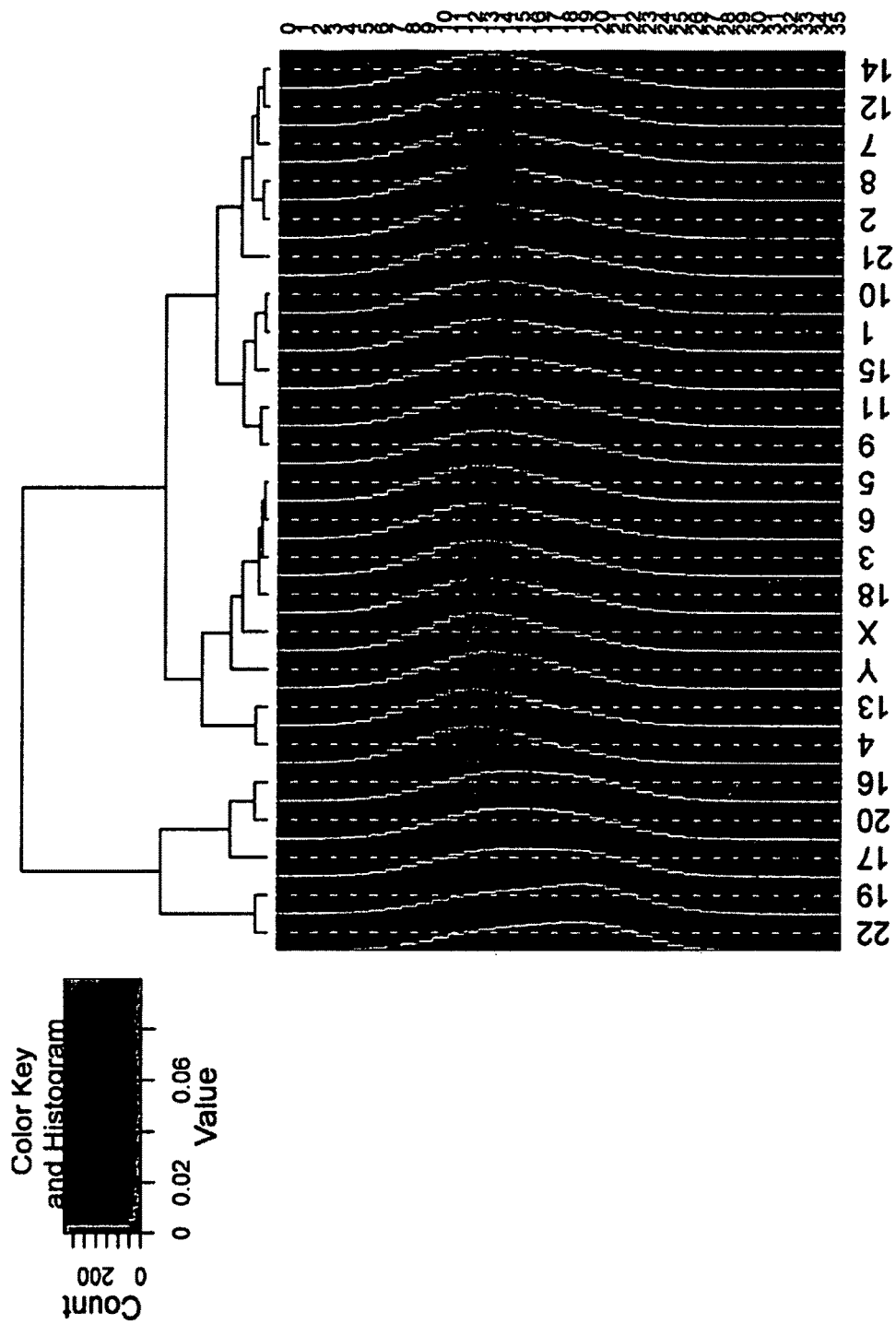
FIG. 4 shows different compositions of GC class for each chromosome. The GC content of every 35 bp read of the reference unique reads was calculated for each chromosome, GC content was classified into 36 levels and the percentage of each level was calculated as the composition GC of each chromosome. The chromosomes were then graphed by the heatmap and clustered hierarchically.
Figure 5A:
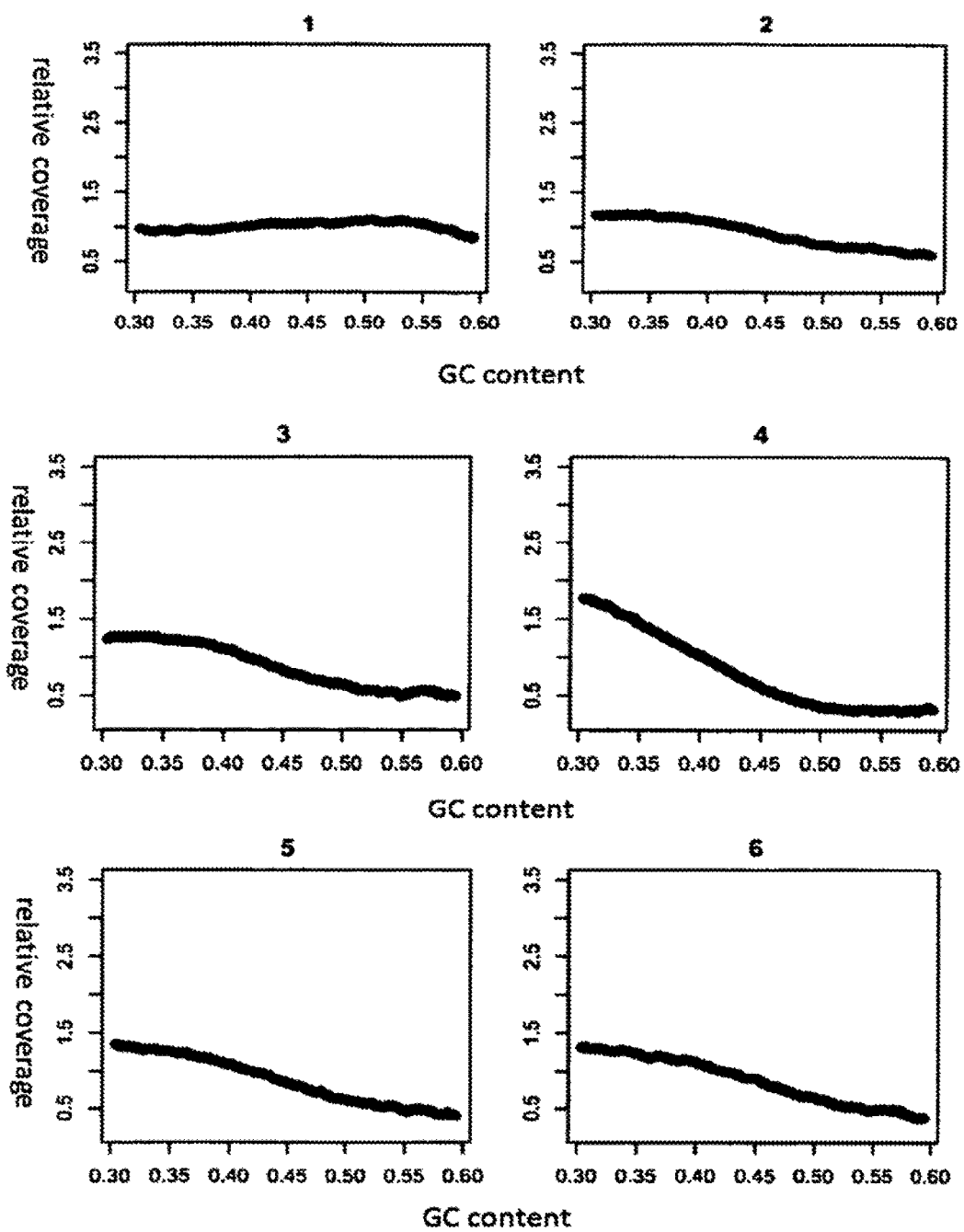
FIGS. 5A-D demonstrate sequencing bias introduces the correlation showed in FIGS. 2A-D by manual simulation of the process of sequencer preference.
Figure 5B:
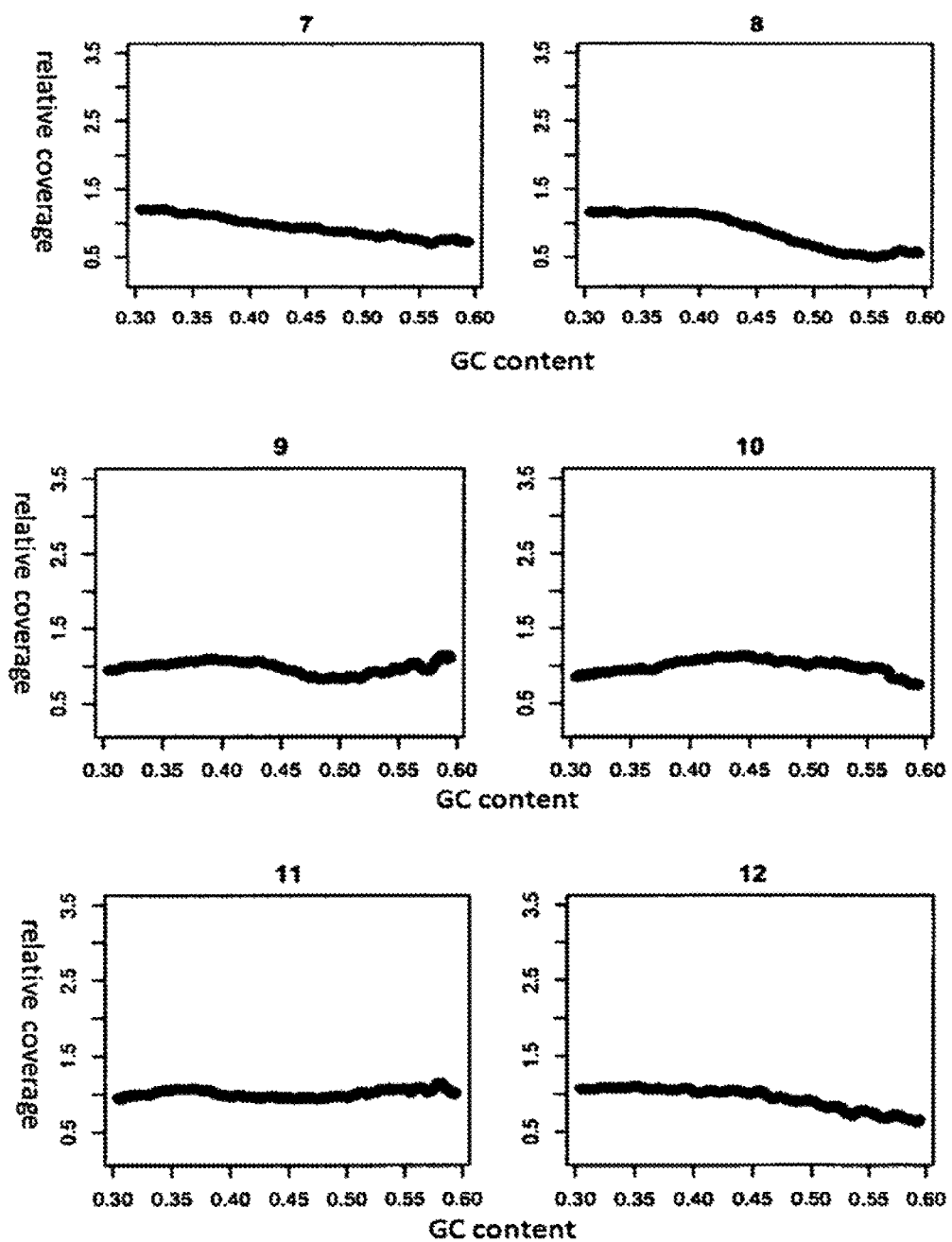
Figure 5C:
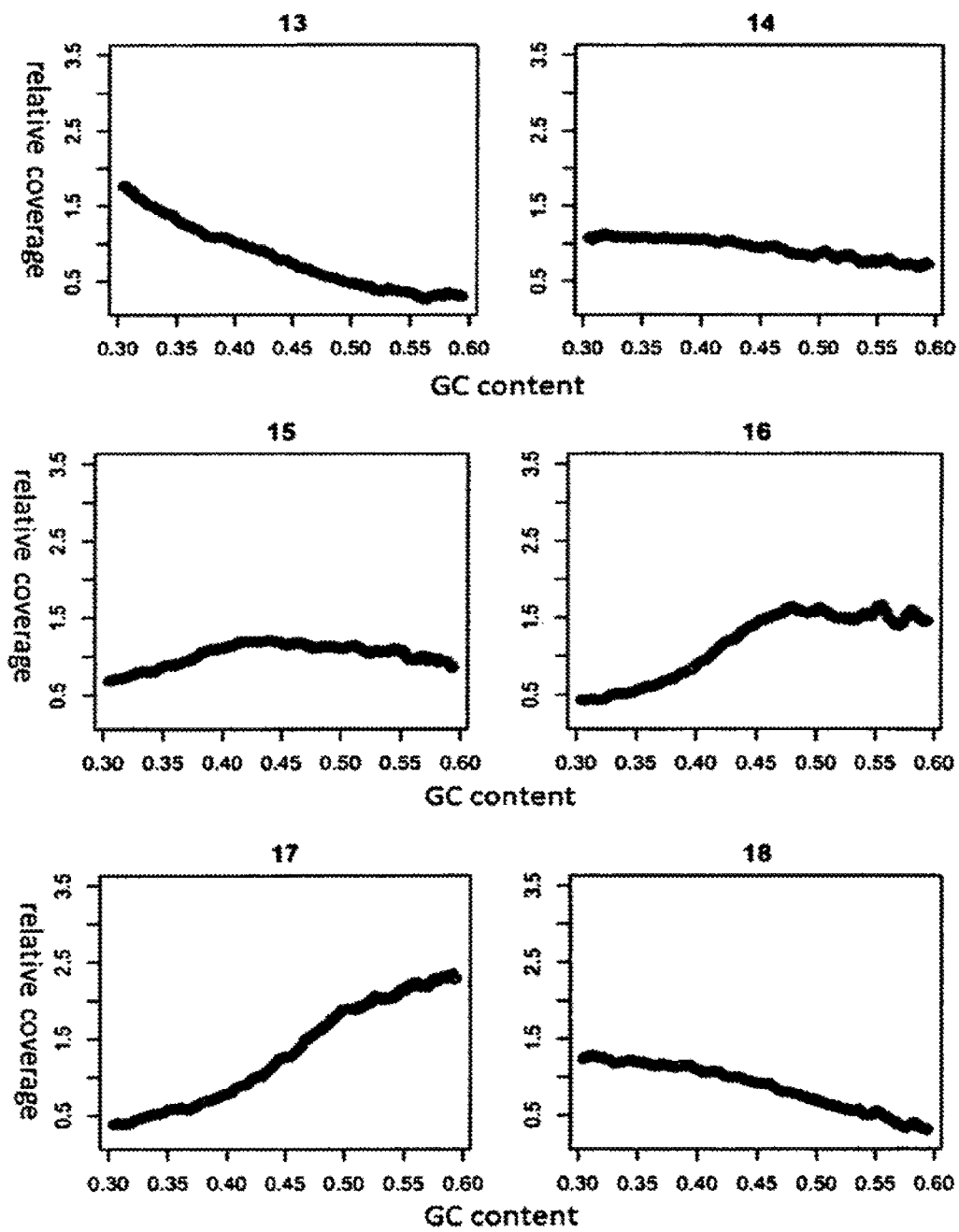
Figure 5D:
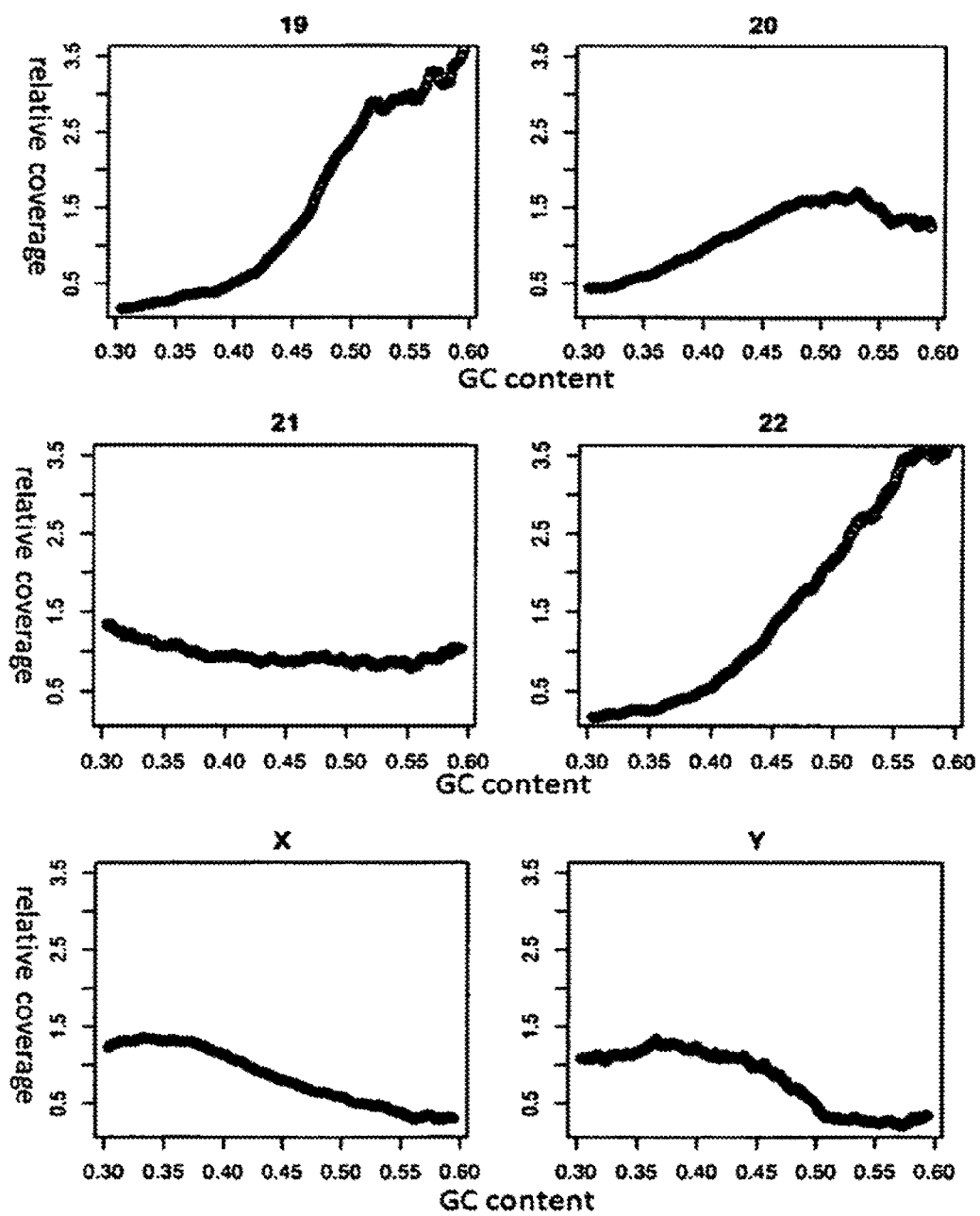
Figure 6A:
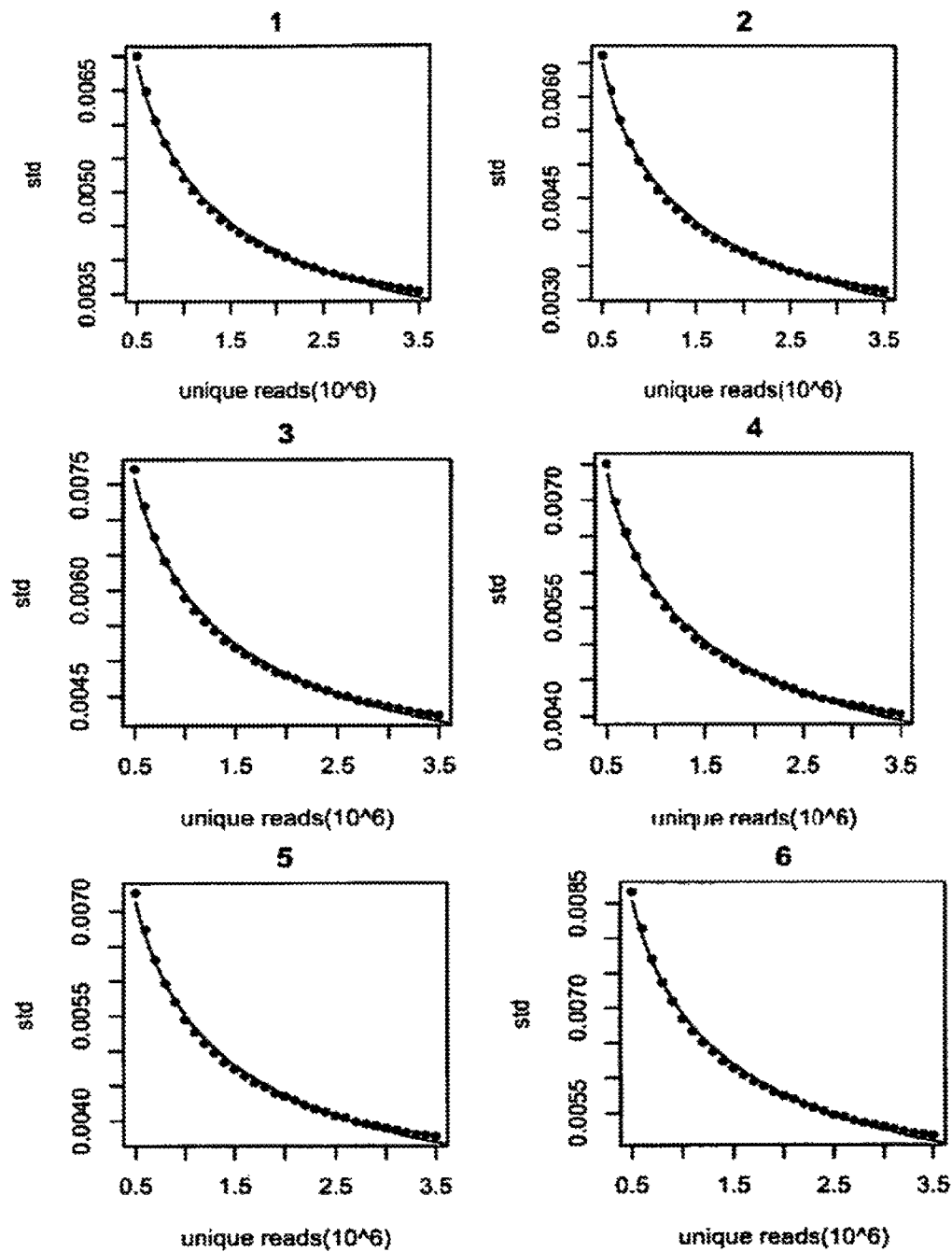
FIGS. 6A-D plot standard variation against total number of sequenced polynucleotide fragments. In 150 samples, the adjusted standard variance of every chromosome shows linear relationship with reciprocal of the square root of the number of unique reads.
Figure 6B:
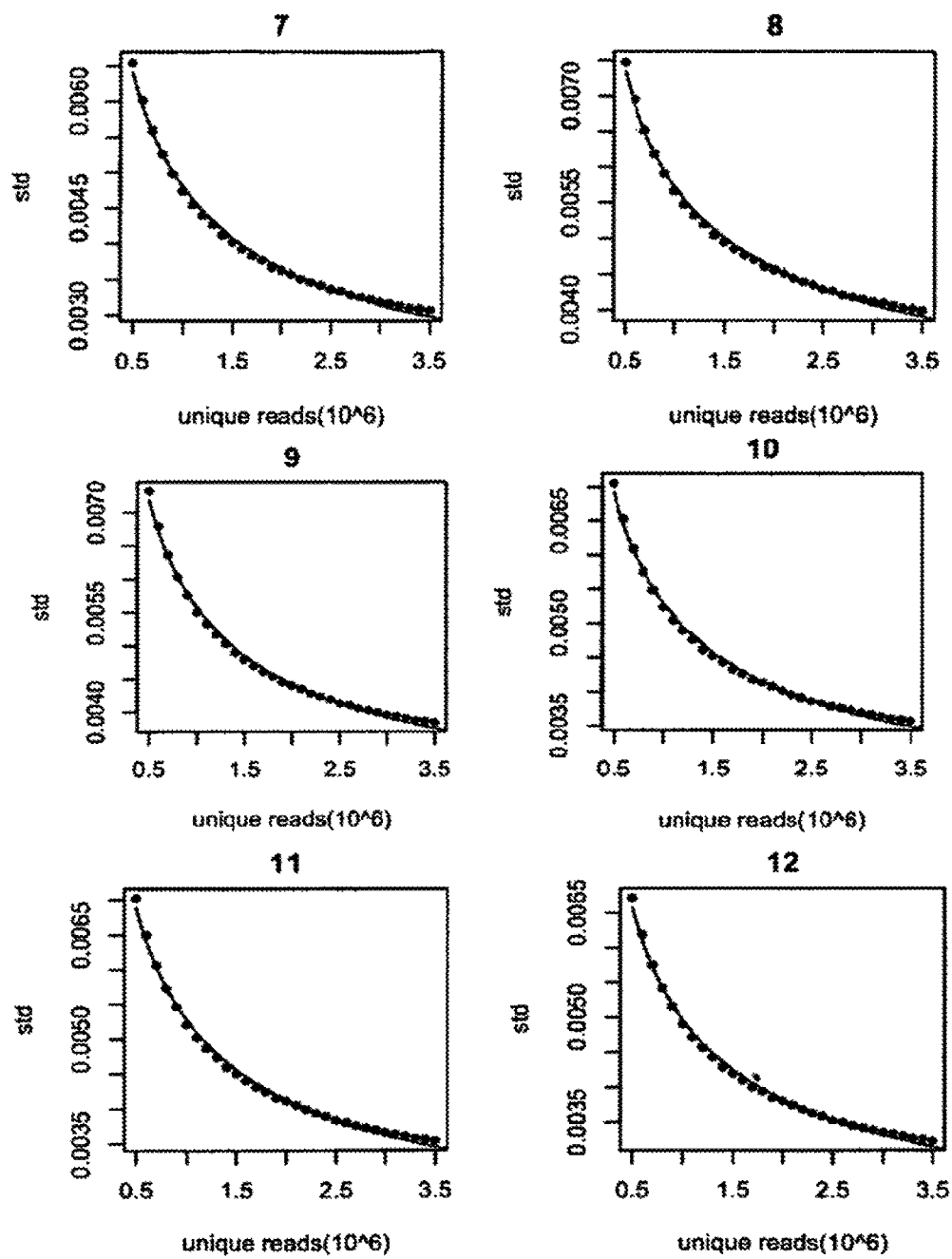
Figure 6C:
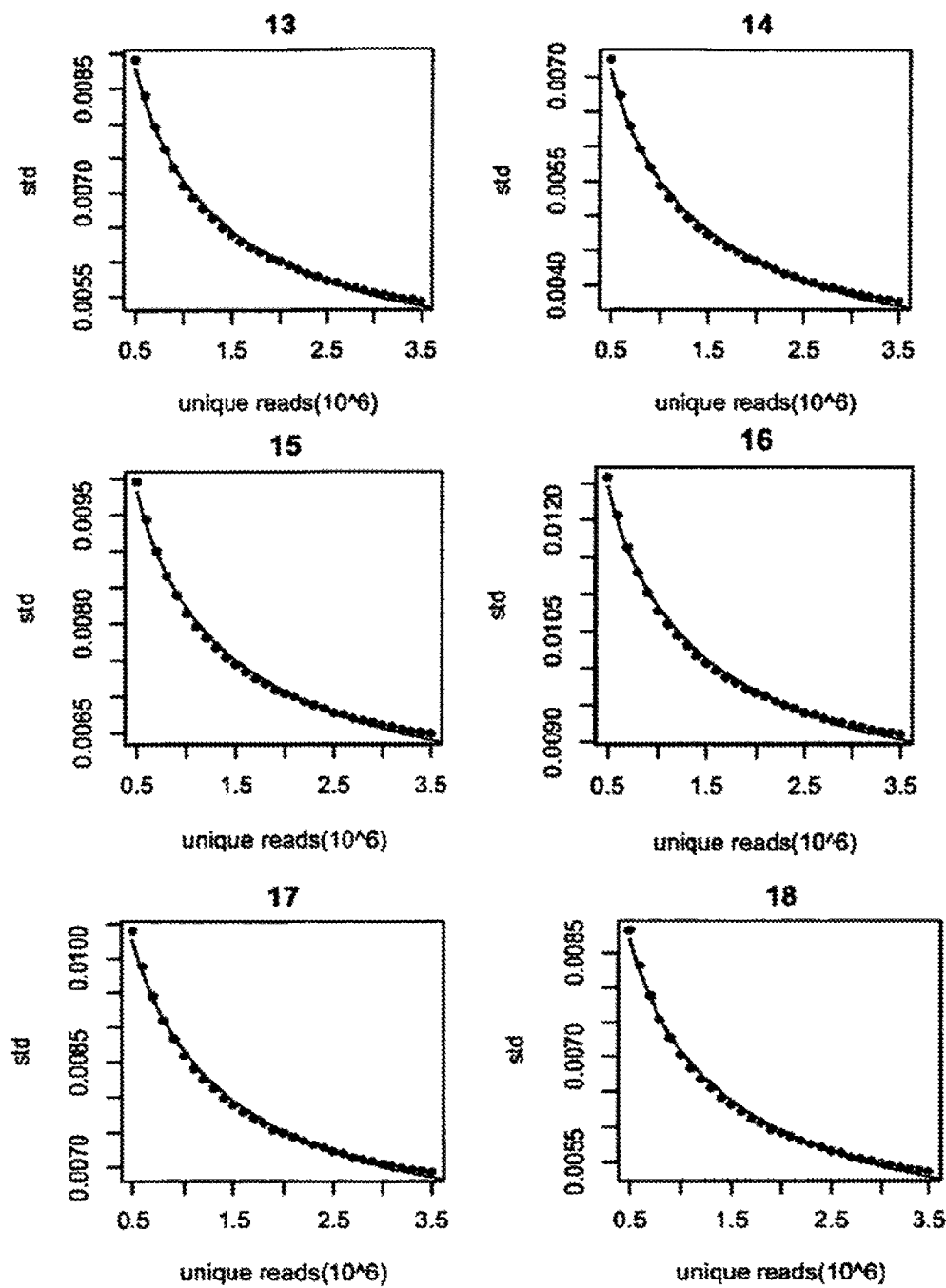
Figure 6D:
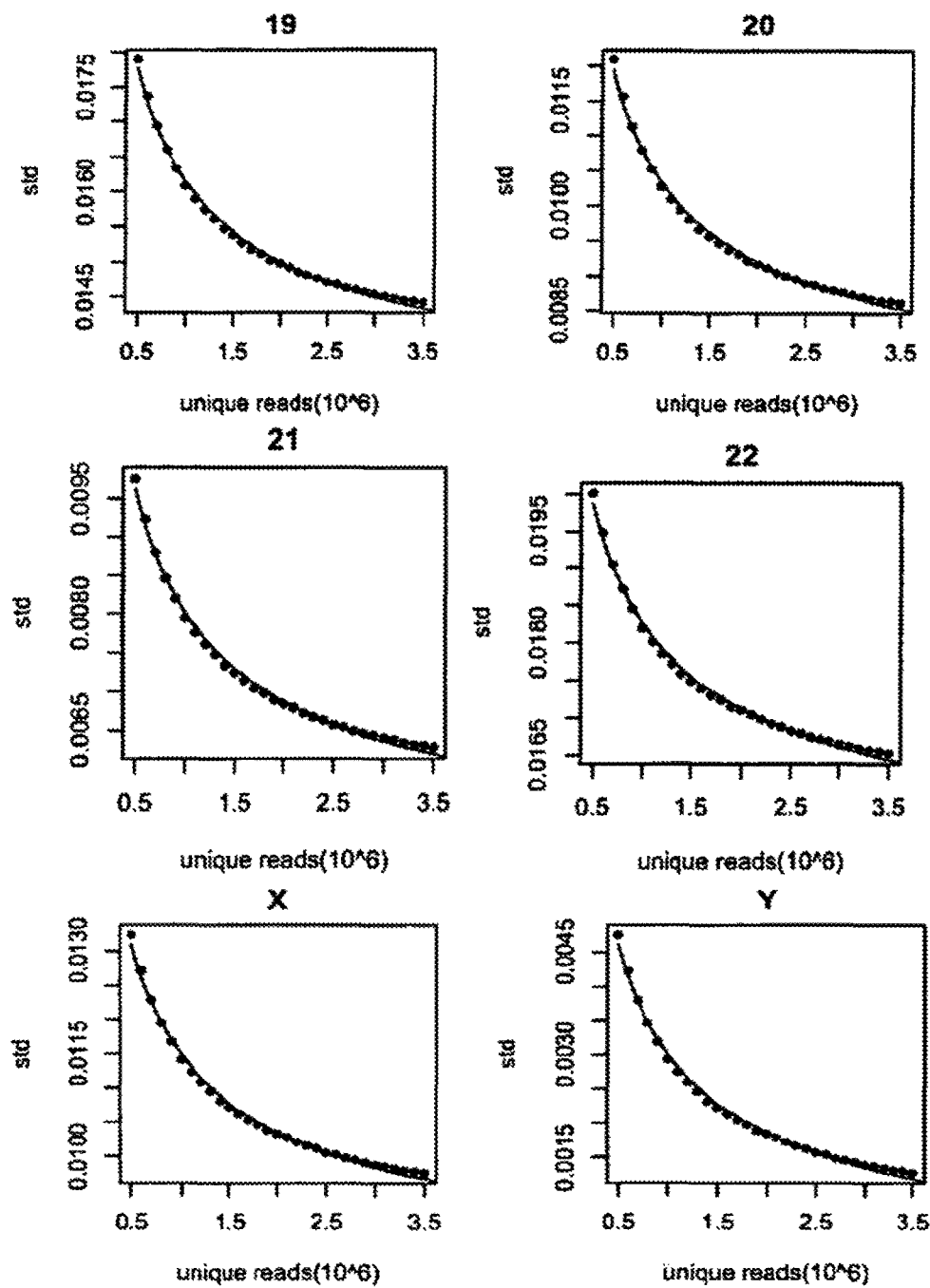

The possible explanation for such a different changing tendency among different GC-content chromosomes is the differences in GC-content composition in different chromosomes shown in FIG. 4 combined with the GC-bias introduced in the sequencing process. The GC content of every 35-mer reference unique reads for each chromosome is used to classify GC content into 36 levels. The percentage of each level as the composition GC of each chromosome was calculated and then used to draw the heatmap with the Heatmap2 software. Take chromosome 13 as an example, large part of it consists of lower GC-content sequence segments but small part of it consists of higher GC-content sequence segments. If conditions during the sequencing or PCR process is in favor of sequence those segment with higher GC-content, then a relative large part of chromosome 13 with low GC-content would be hard to be sequenced with a result that the coverage depth in this sample's chromosome 13 was becoming lower. In comparison, in a higher GC-content group such as chromosome 19, the coverage depth in this sample's chromosome 19 is becoming higher for that a large part of chromosome 19 was of higher GC-content to which the sequencer prefers. No matter in which chromosome, GC-poor and GC-rich segments were hard to be sequenced but the influence introduced by GC-bias was different to different chromosomes with different GC-content composition. Every reference chromosome was divided into 1 KB bins, the GC content of each unique reference read in the bin was calculated. The GC content of each bin in the proper interval form [0.3, 0.6] divided by step size of 0.001, and the relative coverage in every interval is calculated. FIG. 5 shows plots of relative coverage and GC content for each chromosome.

Influence of fetal gender on data was analyzed using independent two-sample t-test. No significant difference was found between autosomes except for sex chromosomes in the same GC content roughly, but there is obvious difference in UR % between female and male (Chiu et al., (2008) *Proc Natl Acad Sci USA* 105:20458-20463), implying that there is no need to distinguish fetal gender when to detect autosome aneuploidy, but it is needed to distinguish fetal gender firstly, when to detect sex chromosome aneuploidy such as XO, XYY etc.

Example 2

Statistical Model

Using this phenomenon discussed above, we tried to use local polynomial to fit the relationship between coverage depth and the corresponding GC content. The coverage depth consists of a function of GC and a residual of normal distribution as following:

$$cr_{i,j} = f(GC_{i,j}) + \epsilon_{i,j}, j=1,2,\ldots,22,X,Y \quad (4)$$

wherein $f(GC_{i,j})$ represents the function for the relationship between coverage depth and the corresponding GC content of sample i, chromosome j, $\epsilon_{i,j}$ represents the residual of sample i, chromosome j.

There is non-strong linear relationship between the coverage depth and the corresponding GC content so we applied loess algorithm to fit the coverage depth with the corresponding GC content, from which we calculated a value important to our model, that is, the fitted coverage depth:

$$c\hat{r}_{i,j} = f(GC_{i,j}), j=1,2,\ldots,22,X,Y \quad (5)$$

With the fitted coverage depth, the standard variance and the student t were calculated according to the flowing Formula 6 and Formula 7:

$$std_j = \sqrt{\sum_i (cr_{i,j} - c\hat{r}_{i,j})^2/(ns-1)}, j=1,2,\ldots,22,X,Y \quad (6)$$

$$t1_{i,j} = (cr_{i,j} - c\hat{r}_{i,j})/std_j, \quad (7)$$
$$j=1,2,\ldots,22,X,Y$$

Example 3

Fetal Fraction Estimation

For the reason that fetal fraction is very important for our detection so we estimated the fetal fraction before the testing procedure. As we had mentioned before, we had sequenced 19 male adults, when compared their coverage depth with that of cases carrying female fetus, we found that male's coverage depth of chromosome X is almost ½ times of female's, and male's coverage depth of chromosome Y is almost 0.5 larger than female's. Then we can estimate the fetal fraction depending on the coverage depth of chromosome X and Y as Formula 8, Formula 9 and Formula 10, considering GC-correlation as well:

$$fy_i = (cr_{i,Y} - c\hat{r}_{i,Yf})/(c\hat{r}_{i,Ym} - c\hat{r}_{i,Yf}) \quad (8)$$

$$fx_i = (cr_{i,X} - c\hat{r}_{i,Xf})/(c\hat{r}_{i,Xm} - c\hat{r}_{i,Xf}) \quad (9)$$

$$fxy_i = \arg\min_{\varepsilon \in (0,1)} \left( \frac{(c\hat{r}_{i,Xf} \cdot (1-\varepsilon) + c\hat{r}_{i,Xm} \cdot \varepsilon - cr_{i,X})^2}{(\hat{\sigma}_{X,f} \cdot (1-\varepsilon))^2 + (\hat{\sigma}_{X,m} \cdot \varepsilon)^2} + \frac{(c\hat{r}_{i,Yf} \cdot (1-\varepsilon) + c\hat{r}_{i,Ym} \cdot \varepsilon - cr_{i,X})^2}{(\hat{\sigma}_{Y,f} \cdot (1-\varepsilon))^2 + (\hat{\sigma}_{Y,m} \cdot \varepsilon)^2} \right) \quad (10)$$

wherein $c\hat{r}_{i,Xf} = f(GC_{i,Xf})$ is the fitted coverage depth by the regression correlation of the chromosome X coverage depth and corresponding GC content of cases with female fetus, $c\hat{r}_{i,Yf} = f(GC_{i,Yf})$ refers to the fitted coverage depth by the regression correlation of the chromosome Y coverage depth and corresponding GC content of cases with female fetus, $c\hat{r}_{i,Xm} = f(GC_{i,Xm})$ refers to the fitted coverage depth by the regression correlation of the chromosome X coverage depth and corresponding GC content of male adults $c\hat{r}_{i,Ym} = f(GC_{i,Ym})$ refers to the fitted coverage depth by the regression correlation of the chromosome Y coverage depth and corresponding GC content of male adults. For computing simply, given $\hat{\sigma}_{X,f}$ and $\hat{\sigma}_{X,m}$ are equal and $\hat{\sigma}_{Y,f}$ and $\hat{\sigma}_{Y,m}$ are equal.

Example 4

Calculation of Residual of Every Chromosome

FIG. 6 shows that the standard variation (see Formula 3) for every chromosome under a certain total number of unique reads is influenced by the participating cases number of the reference. The standard variation barely increases when the selected cases number was more than 150 under the condition that 1.7 million of total unique reads number were sequenced for each case. However, the standard variation was different for different chromosomes. After considering the GC-bias, our method had a moderate standard variation for chromosome 13 (0.0063), chromosome 18 (0.0066) and chromosome 21 (0.0072). The standard variation of chromosome X is higher than above mentioned chromosomes which would require more strategies to do accurate abnormal detection.

Figure 7A:
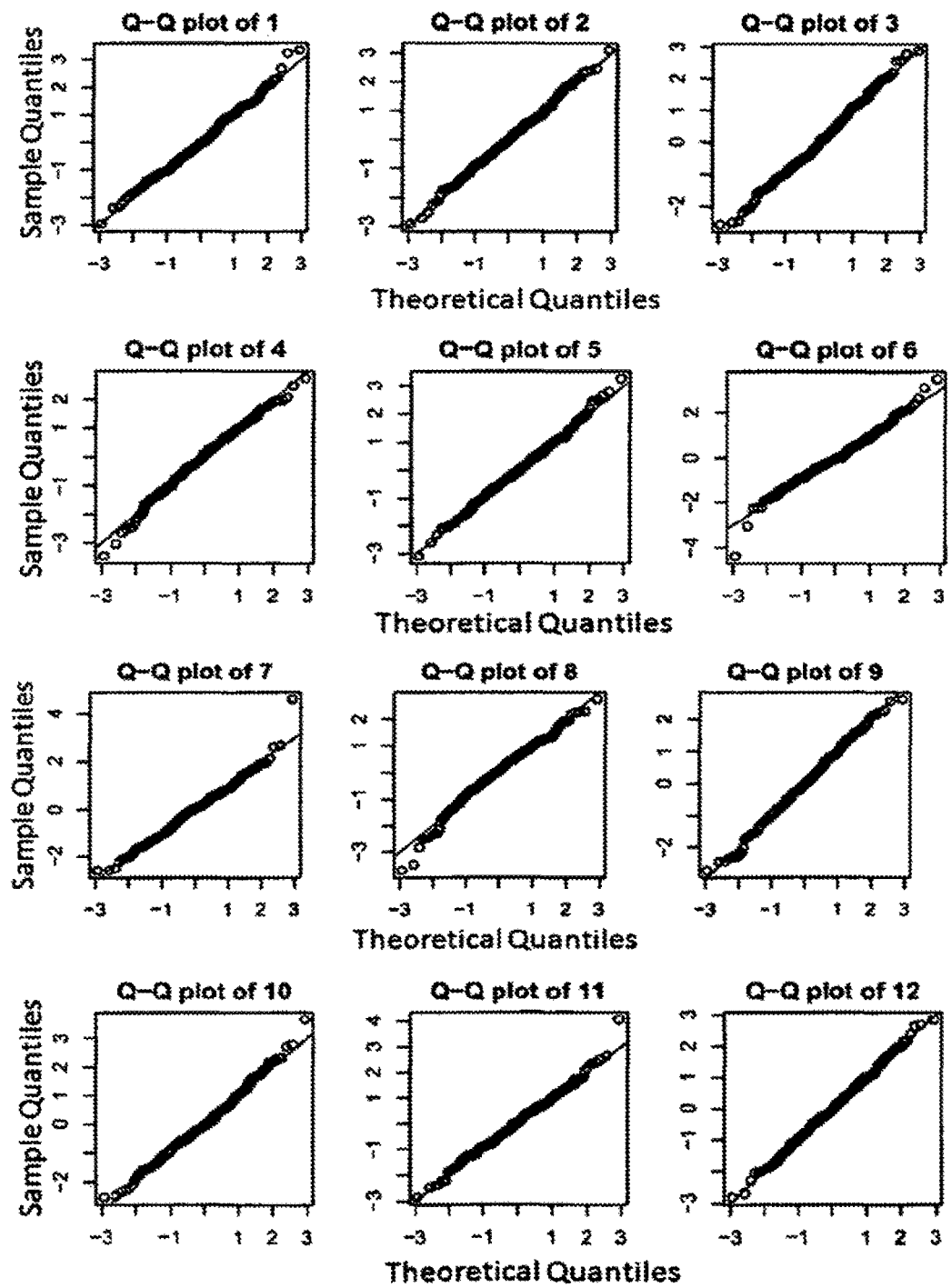
FIGS. 7A-B show plots of residual of every chromosome calculated by Formula 3. A linear relationship is shown with a normal distribution.
Figure 7B:
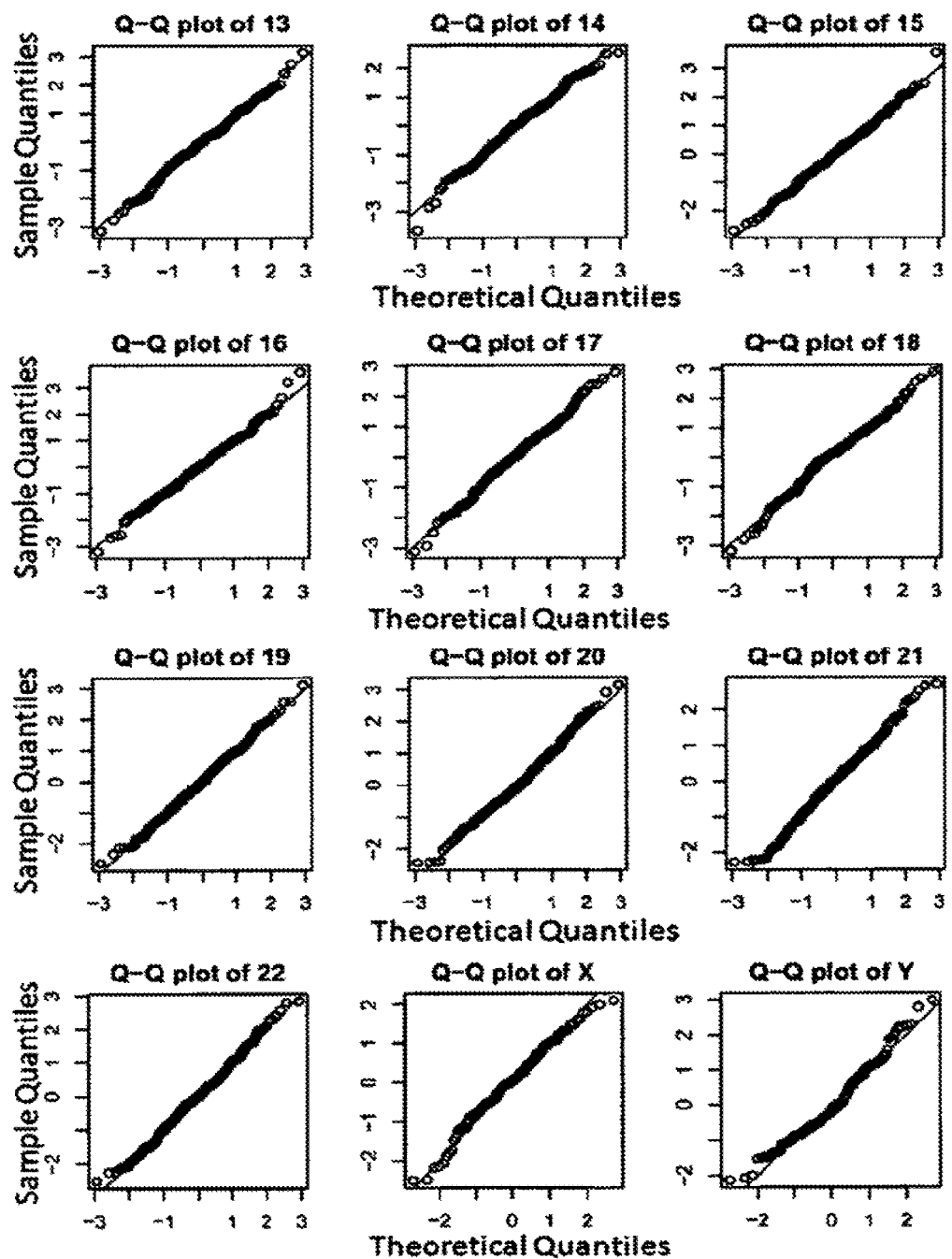

FIG. 7 shows the Q-Q plot, wherein the residual is compiled to normal distribution which implicates the student-t calculation is reasonable.

Example 5

The Distinguishing of Fetal Gender

To discover the disorder of the sex chromosome, it is best to distinguish fetal gender. There existed two obvious peaks when we investigated the frequency distribution of the coverage depth of chromosome Y in our 300 cases, which gave us a hint to distinguish the gender by coverage depth of chromosome Y. Cases with coverage depth less than 0.04 can be regarded as carrying female fetus while more than 0.051 regarded as carrying male fetus, between 0.04 and 0.051 are regarded as gender uncertain as FIG. 8. For these gender dubious and aneuploidy cases, logistic regression was used to predict their gender as Formula II (Fan, et al., *Proc Natl Acad Sci USA* (2008) 42:16266-16271):

$$logit(p_i) = \ln\left(\frac{p_i}{1-p_i}\right) = \beta_0 + \beta_1 cr.a_{i,x} + \beta_2 cr.a_{i,y} \quad (11)$$

wherein $cr \cdot a_{i,x}$ and $cr \cdot a_{i,y}$ are normalized relative coverage of X and Y, respectively.

Comparing with the karyotype result, our method for distinguishing fetal gender performed quite well in our 300 reference cases with 100% accuracy while mistook one case when being carried out in our 901 cases set and the chromosome Y coverage depth of this mistaken case is between 0.04 and 0.051.

Example 6

Diagnostic Performance of GC-Correlation t-Test Approach

Sample Recruitment 903 participants were recruited prospectively from Shenzhen People's Hospital and Shenzhen Maternal and child care service center with their karyotype results. Approvals were obtained from the institutional review boards of each recruitment site and all participants gave informed written consent. The maternal ages and gestational weeks at blood sampling were recorded. The 903 cases included 2 trisomy 13 cases, 15 trisomy 18 cases, 16 trisomy 21 cases, 3 XO cases, 2 XXY cases and 1 XYY cases. Their karyotype results distribution is shown in FIG. 9.

Maternal Plasma DNA Sequencing

Peripheral venous blood (5 milliliters) was collected from each participating pregnant woman in EDTA tubes and centrifuged at 1,600 g for 10 min in 4 hours. Plasma was transferred to microcentrifuge tubes and recentrifuged at 16,000g for 10 min to remove residual cells. Cell-free plasma was stored at 80° C. until DNA extraction. Each plasma sample was frozen and thawed only once.

For massively parallel genomic sequencing, all extracted DNA from 600 µl maternal plasma was used for DNA library construction according to a modified protocol from Illumina. Briefly, end-repairing of maternal plasma DNA fragments was performed using T4 DNA polymerase, Klenow™ polymerase, and T4 polynucleotide kinase. Commercially available adapters (Illumina) were ligated to the DNA fragments after addition of terminal A-residues. The adapter-ligated DNA was then additionally amplified using a 17-cycle PCR with standard multiplex primers. Agencourt AMPure™ 60 ml Kit (Beckman) was used for the purification of PCR products. The size distribution of the sequencing libraries was analyzed with a DNA 1000 kit on the 2100 Bioanalyzer™ (Agilent) and quantified with Real-time PCR. The sequencing libraries with different index were then pooled into one by equal quantity before cluster station on Illumina GA II™ (single-end sequencing).

19 male euploid samples were sequenced for subsequent analysis for estimation of fetal DNA fraction. One new GC-correlation t-test approach has been developed by us for the diagnosis of trisomy 13, trisomy 18, trisomy 21 and sex-chromosome abnormities. And we compared this new method to other two methods mentioned below in terms of diagnostic performance.

Example 7

Detection of Fetal Aneuploidy Such as Trisomy 13, 18 and 21

To determine whether the copy number of a chromosome within a patient case deviated from normal, the coverage depth of a chromosome was compared to that of all other reference cases. All previous study had just one null hypothesis. We introduced binary hypotheses for the first time by using a two null hypothesis. One null hypothesis (H0: the fetus is euploidy) was the assumption that the mean coverage depth of the patient case distribution and the mean coverage depth of all normal reference distribution were equal, which means that the patient case was euploid if this null hypothesis is accepted. Using student t test, t1 can be calculated as Formula 12:

$$t1_{i,j} = (cr_{i,j} - cf_{i,j})/std_j \quad (12)$$

The other null hypothesis (H1: the fetus is aneuploidy) was that the mean coverage depth of the patient case distribution with a rough fetal fraction was equal to the mean coverage depth of the distribution of aneuploidy cases with the same fetal fraction, which means that this patient case is aneuploid if this null hypothesis were accepted. The student t-statistic, t2 were calculated as Formula 13:

$$t2_{i,j} = (cr_{i,j} - cf_{i,j}(1+fxy_{i,j}/2)))/std_j \quad (13)$$

|t1|>3 and |t2|<3 would indicate an aneuploid case in most instances especially when the distributions between euploid cases and aneuploid cases were completely discriminated, while in other condition such as the insufficient precision or insufficient fetal fraction and so on, |t1| may smaller than 3 but the fetus was abnormal. Combined t1 and t2 can help us make more accurate decision, then we employed Log likelihood ratio of t1 and t2 as Formula 14:

$$L_{i,j} = \log(p(t1_{i,j}, degree|D))/\log(p(t2_{i,j}, degree|T)) \quad (14)$$

wherein $L_{i,j}$ is Log likelihood ratio. If the ratio was larger than 1, we could infer the fetus might be trisomy.

But for cases with female fetuses, it is hard for us to estimate its fetal fraction so that is impossible to compute. However, we can give a Reference Value (RV) of fraction 7% according to the empirical distribution of fetal fraction.

903 cases were investigated, 866 of them carried euploid fetuses amongst which 300 cases had been selected out randomly to develop the GC correlation student-t approach. Besides, 2 trisomy 13, 12 trisomy 18, 16 trisomy 21, 4 XO (consisting of 3 XO cases, and 1 chimera 45, xo/46, xx (27:23) case), 2 XXY and 1XYY case were participated in our study. After alignment, we obtained a mean of 1.7 Million of data (SD=306185) unique aligned reads per case with no mismatch. By using our newly developed GC-correlation student t test, all the T13 cases (2 out of 2) were successfully identified, while 901 out of 901 non-trisomy 13 cases were correctly classified (FIG. 10A). The sensitivity and specificity of this approach were 100% and 100% (Table 1).

For trisomy 18, 12 out of 12 trisomy 18 cases and 888 out of 891 non-trisomy 18 cases could be correctly identified (FIG. 10A). The sensitivity and specificity of this approach were 100% and 99.66% respectively. For trisomy 21, 16 out of 16 trisomy 21 cases and 16 out of 16 non-trisomy 21 cases could also be correctly detected (FIG. 10A). The sensitivity and specificity of this approach were 100% and 100% respectively.

Example 8

Detection of XO, XXX, XXY, XYY

Above we considered the detection of trisomy for autosomes, disorders for sex chromosome such as XO, XXX, XXY and XYY can be detect by our method, too.

correctly classified (FIG. 10B) with the sensitivity 100% and specificity 100%. For the XYY case, we identified it correctly (FIG. 10B) and the sensitivity and specificity were 100% and 100% respectively.

To evaluate whether our novel approach had any advantages when compared to other two reported approaches, z-score and z-score with GC correction, we implemented all these three approaches to analyze our 900 cases and the same 300 cases as reference set for all those approaches. The precision of a measurement was always embodied in the confidence value (CV). In our investigation, the CV of standard z-score approach is larger than the other approaches in clinically interested chromosome 18 and 21 (FIG. 11) leading to a lower sensitivity rate for trisomy 18 and 21 (Table 1).

TABLE 1

Comparison of sensitivity and specificity of different methods

|  |  | Standard z-score approach | | z-score approach with GC correction | | our approach with GC correlation t-test | |
| --- | --- | --- | --- | --- | --- | --- | --- |
|  | Diagnosis (# of cases) | Sensitivity (%) | Specificity (%) | Sensitivity (%) | Specificity (%) | Sensitivity (%) | Specificity (%) |
| Autosome | Trisomy 13 (2) | 50% | 99.89 | 100% | 100% | 100% | 100% |
|  | Trisomy 18 (12) | 91.67% | 100% | 100% | 99.89% | 100% | 99.96% |
|  | Trisomy 21 (16) | 93.75% | 100% | 100% | 100% | 100% | 100% |
| Heterosome | XO (3 XO, 1 XO/XX chimera) | not available | not available | not available | not available | 75% | 100% |
|  | XXY (1) | not available | not available | not available | not available | 100% | 100% |
|  | XXY (2) | not available | not available | not available | not available | 100% | 100% |
| Binary hypothesis | | not available | | not available | | available | |

Firstly, gender was confirmed by gender distinguishing. If a testing case was confirmed to carry female fetus, student-t value t1 $t1_{i,X} = (cr_{i,X} - \hat{cr}_{i,Xf})/std_{Xf}$ was needed to be calculated for XXX or XO detection, where $\hat{cr}_{i,Xf}$ and $std_{Xf}$ are same as Formula 10; if t1 is larger than 3.13 or less than −3.13, this case may be XXX or XO. But considering precision was limited by the great deviation of coverage depth for chromosome X, we sampled the plasma again and repeated the experiment to make a more credible decision when |t1|<5 even though |t1|>3.13. |t1|>5 was confirmed to be aneuploidy in this case. All our detection processes were on the premise that the data satisfied the standard quality control.

If the testing sample was confirmed to carry with male fetus, the fetal DNA fraction was estimated first by Y and X. Meanwhile, we could extrapolate the fitted coverage depth for chromosome X with the fetal DNA fraction estimated only by the coverage depth of chromosome Y and t2 can be calculated. $t2_i = (cr_{i,X} - (1 - fy_i/2) \cdot \hat{cr}_{i,Xf})/std_{Xf}$. If t2 is too large (larger than 5) or too small (less than −5) the fetus may be XXY or XYY. In addition, the gap between fetal fractions estimated by X and Y independently will provide information for detecting disorders about sex chromosomes.

In the XO detection, 3 out of 4 XO cases were detected, and the case failed to be identified was a chimera case (FIG. 10B). The sensitivity and specificity of this approach were 75% (100% if we disregard the chimera case) and 99.55% respectively. For XXY cases, all the 2 cases were successfully identified, while 901 out of 901 non-XXY cases were For the z-score approach with GC correction, the CV value of chromosome 13 is 0.0066 with 100% sensitivity rate and 100% specificity rate. For the novel GC correlation student t approach discussed herein, the CV value of chromosome 13 is 0.0063 and with 100% sensitivity rate and 100% specificity rate. In chromosome 18, the CV of these two approaches were 0.0062 and 0.0066, respectively, both with 100% sensitivity and specificity rates for them were 99.89% and 99.96%, respectively. The performance was similar when comparing the CV of these two approaches for chromosome 21: 0.0088 and 0.0072, respectively. Both resulted in the same sensitivity rate of 100% in our small cases set study and achieved the same 100% specificity rate. And these two methods all performed better than the standard z-score approach. Not only was our new developed approach with GC correlation comparable to the GC correction approach with good performance, but also it had another advantage in the detection of sex-chromosome abnormalities such as XO, XXY and XYY. Our data shows that when process GC correction approach there would be difficult to distinguish fetuses' gender by deviation of data represent sex chromosomes introduced in amending the number of sequence tags by multiplying a weight factor so that the detection of sex chromosome disorder seemed to be hard.

Example 9

Theoretical Performance of GC-Correlation t-Test Approach in Consideration of Data Size, Gestational Weeks and Fetal DNA Fraction Measuring aneuploidy remains challenging because of the high background of maternal DNA (Fan, et al., *Proc Natl Acad Sci USA* (2008) 42:16266-16271) and arbitrary small fetal DNA fraction was the most significant restraining factor for aneuploidy detection by massively parallel genome sequencing (MPGS) approach to this day. However, there was no big breakthrough in determining the minimum fetal DNA fraction clinically before MPGS detection especially for female fetuses while the only clinical clue related to implicate the fraction of fetal DNA was gestational weeks. It was reported that there is a statistically significant correlation between the fetal DNA fraction and gestational age previously (Lo, et al., *Am. J. Human Genet.* (1998) 62:768-775). In our study, to investigate the relationship between estimated fetal DNA fraction and gestational age, we plotted in FIG. 12 the fetal DNA fraction of all those participating cases with male fetuses (totally 427 cases) referred to estimation Formula 10. The estimated fetal DNA fraction for each sample correlates with gestational age (P smaller than 0.0001). It also showed that even though in the gestational age 20, there were 4 out of 65 cases with fetal DNA fraction less than 5%, which would adversely affect the detection accuracy. To evaluate the fetal fraction estimation method we selected some cases hierarchically distributed in estimated fetal fraction, and then Q-PCR helped to calculate another relative fetal fraction. Then we got a correlation standard curve showing a strong correlation between them which demonstrated the estimation of fetal fraction by our method is credible.

Meanwhile, the sequencing depth (the number of total unique reads) was another significant factor affecting the precision of aneuploidy detection embodying in the value of standard variation. The standard variation for each chromosome employed in our GC-correlated approach could be fixed under a certain level of sequencing depth when the reference case number reaches 150 (FIG. 13). To investigate how the sequencing depth influence the standard variation for each chromosome, we sequenced 150 cases not only in our 1.7 million level but in another sequencing depth level with the number of total unique reads reaching 5 million (SD=1.7 million). Depending on these two sets, we found the standard variance is linear with reciprocal of square root of the total unique reads number demonstrated in FIG. 6.

For a given fetal DNA fraction, we could estimate the total unique reads number required in our method to detect deviation of chromosome copy number from normal at t1 equal 3 (FIG. 14). It showed that the less the fetal DNA fraction was, the greater sequencing depth required. In our 1.7 million unique reads set, our approach is able to detect aneuploidy fetuses for chromosome 13 and X with fetal DNA fraction more than 4.5% and aneuploidy fetuses for chromosome 21 and 18 more than 4%; while in our 5 million reference set, our approach was capable to detect trisomy 18 and trisomy 21 even with the fetal DNA fraction about 3%. If we want to identify fetuses abnormal in chromosome X such as XXX or XO with the fetal fraction about 4%, the required total unique number in those cases and corresponding reference cases should reach 5 million. If the fetal DNA is less than 3.5%, the sequencing depth requirement would beyond 20M. And if the DNA fetal fraction was lower the detection would become incredible and difficult so we proposed another strategy, that is, we should re-sampling the pregnant woman's plasma, re-do our experiment and re-analyze the data when the gestational age become larger on the great probability that fetal DNA fraction would be elevated along with the increasing of gestational age. And this strategy also can be applied to samples suspected to have small fetal DNA fraction.

Even though our approach performs well but it is not persuasive without a large set of abnormal cases. To estimate the sensitivity of this GC-correlation student t approach applying by us, we published the theoretical sensitivity considering different gestational age and different sequencing depth.

We calculated the theoretical sensitivity of aneuploidy with following steps. Firstly, we applied regression analysis to fit fetal DNA fraction with gestational age $\hat{fr}_i=f(gsa_i)$, where $\hat{fr}_i$ is the fitting mean of fetal DNA fraction in ith gestational age $gsa_i$, and estimated the approximate fetal DNA fraction distribution by employing Gaussian kernel density estimation (Birke, (2008) *Journal of Statistical Planning and Inference* 139:2851-2862) mainly referring to estimated fetal DNA fraction distributed in 19 and 20 gestational weeks before extrapolating the fetal DNA fraction distribution in the other weeks according to the relationship between fetal DNA fraction and gestational age $$\hat{pd}_i(x) = \frac{1}{nh}\sum_{i=1}^{n} K\left(\frac{x-X_i}{h}\right) + \left(\hat{fr}_i - \frac{fr_{19}+fr_{20}}{2}\right),$$

where $\hat{pd}_i$ is the fitting probability density of fetal DNA fraction in ith gestational age, where X is data of 19 and 20 gestational weeks (FIG. 12). Secondly, we estimated the standard variance according to total unique reads number as we mentioned before $\hat{\sigma}=f(tuqn)$ where tuqn is total unique reads number. Finally, to calculate the sensitivity in every gestational age at a certain sequencing depth level according to the fetal DNA fraction distribution and standard variance estimated in each sequencing depth, we computed the probability density of false negative in every fetal DNA fraction (here, we supposed that the fetal DNA fraction fluctuation normally distributed) and then integrated them to get a false negative rate (FNR) in a gestational age consisting of all levels of fetal DNA fraction FNR(fr, week)=$\int_0^1 pd(fr)\int_0^{\alpha/\sigma_j=3} \exp(x-fr)^2/2\cdot\sigma_j^2 dxdfr$ where j is chromosome j. Easily, the theoretical sensitivity in a certain sequencing depth in this gestational age is calculated as 1-FNR. FIGS. 15-21 show the resulting plots of our calculation. The student-t larger than 3 was set to identify female fetus aneuploidy while for male fetus, when computing probability density of false negative in every fraction, a logarithm likelihood larger than 1 was employed as the critical value we mentioned in Binary hypothesis which helped to achieve a higher sensitivity comparing to female ones.

However, our inference is relative conservative for the reason that it is hard to get a distribution infinitely approximate to real distribution of fetal DNA fraction along with gestational age especially in small gestational age in small-scale sampling.

REFERENCES

1. Virginia P. Sybert, Elizabeth McCauley (2004). Turner's Syndrome, *N Engl J Med* (2004) 351:1227-1238.

2. Robert Bock (1993). *Understanding Klinefelter Syndrome: A Guide for XXY Males and Their Families*. NIH Pub. No. 93-3202 August 1993
3. Aksglaede, Lise; Skakkebaek, Niels E.; Juul, Anders (January 2008). "Abnormal sex chromosome constitution and longitudinal growth: serum levels of insulin-like growth factor (IGF)-I, IGF binding protein-3, luteinizing hormone, and testosterone in 109 males with 47,XXY, 47,XYY, or sex-determining region of the Y chromosome (SRY)-positive 46,XX karyotypes". *J Clin Endocrinol Metab* 93 (1): 169-176. doi:10.1210/jc.2007-1426.PMID 17940117.
4. H. Bruce Ostler (2004). *Diseases of the eye and skin: a color atlas*. Lippincott Williams & Wilkins. pp. 72. ISBN 9780781749992.
5. Driscoll D A, Gross S (2009) Clinical practice. Prenatal screening for aneuploidy. *N Engl Med* 360: 2556-2562.
6. Karl O. Kagan, Dave Wright, Catalina Valencia etc (2008). Screening for trisomies 21, 18 and 13 bp maternal age, fetal nuchal translucency, fetal heart rate, free b-hCG and pregnancy-associated plasma protein-A. *Human Reproduction* Vol. 23, No. 9 pp. 1968-1975, 2008 doi: 10.1093/humrep/den224
7. Malone F D, et al. (2005) First-trimester or second-trimester screening, or both, for Down's syndrome. *N Engl J Med* 353:2001-2011.
8. Fan H C, Quake S R (2010) Sensitivity of Noninvasive Prenatal Detection of Fetal Aneuploidy from Maternal Plasma Using Shotgun Sequencing Is Limited Only by Counting Statistics. *PLoS ONE* 5(5): e10439. doi: 10.1371/journal.pone.0010439.
9. Chiu R W, Chan K C, Gao Y, Lau V Y, Zheng W, et al. (2008) Noninvasive prenatal diagnosis of fetal chromosomal aneuploidy by massively parallel genomic sequencing of DNA in maternal plasma. *Proc Natl Acad Sci USA* 105: 20458-20463.
10. McCullagh, P. and Nelder, J. A. (1989), *Generalized Linear Models*, London, UK: Chapman & Hall/CRC.
11. Fan H C, Blumenfeld Y J, et al. (2008) Noninvasive diagnosis of fetal aneuploidy by shotgun sequencing DNA from maternal blood. *Proc Natl Acad Sci USA* 42:16266-16271.
12. Melanie Birke. (2008) Shape constrained kernel density estimation. *Journal of Statistical Planning and Inference* Volume 139, Issue 8, 1 Aug. 2009, Pages 2851-2862.
13. Lo et al., *Lancet* 350:485 487 (1997).
14. Lo et al., *Am. J. hum. Genet.* 62:768-775 (1998).
15. Pertl and Bianchi, *Obstetrics and Gynecology* 98:483-490 (2001).
16. Rogers and Ventner, "Genomics: Massively parallel sequencing," *Nature,* 437, 326-327 (15 Sep. 2005).
17. Mewar et al., "Clinical and molecular evaluation of four patients with partial duplications of the long arm of chromosome 18," *Am J Hum Genet.* 1993 December; 53(6):1269-78.
18. Margulies et al., (2005) *Nature* 437:376-380.
19. Harris et al., (2008) *Science,* 320:106-109.
20. Soni and Meller, (2007) *Clin Chem* 53:1996-2001.
21. Dear, (2003) *Brief Funct Genomic Proteomic* 1:397-416.

We claim:
1. A method to determine a fetal chromosomal abnormality, which method comprises:
 a) obtaining sequence information of multiple polynucleotide fragments from a sample;
 b) assigning said fragments to chromosomes based on said sequence information by comparing the sequence of the fragments with a reference human genomic sequence;
 c) calculating coverage depth and GC content of a chromosome based on said sequence information, wherein the coverage depth of the chromosome is the ratio between the number of fragments that assigns to said chromosome and the number of Reference Unique Reads of said chromosome, and the GC content of the chromosome is the average GC content of all fragments that assign to said chromosome, wherein the Reference Unique Reads are fragments of a chromosome that have unique sequences each of which is unambiguously assigned to a single chromosomal location;
 d) calculating fitted coverage depth of said chromosome using said GC content of said chromosome and an established relationship between coverage depth and GC content of said chromosome,
 wherein the relationship is in the formula:

$$cr_{i,j} = f(GC_{i,j}) + \epsilon_{i,j}, j=1,2,\ldots, 22, X, Y,$$

wherein $f(GC_{i,j})$ represents the function for the relationship between coverage depth and the corresponding GC content of sample i, chromosome j, $\epsilon_{i,j}$ represents the residual of sample i, chromosome j, and
 wherein the fitted coverage depth is calculated according to the formula:

$$c\hat{r}_{i,j} = f(GC_{i,j}), j=1,2,\ldots, 22, X, Y; \text{ and}$$

e) comparing said fitted coverage depth to said coverage depth of said chromosome by a statistical hypothesis test to determine a fetal chromosomal abnormality selected from the group consisting of aneuploidy, polyploidy, monosomy, trisomy, and a sex chromosome abnormality.
2. The method of claim 1, further comprising:
 f) determining the fetal gender.
3. The method of claim 2, wherein the fetal gender is determined according to the formula:

$$logit(p_i) = \ln\left(\frac{p_i}{1-p_i}\right) = \beta_0 + \beta_1 cr.a_{i,x} + \beta_2 cr.a_{i,y},$$

wherein $cr.a_{i,x}$ and $cr.a_{i,y}$ are normalized relative coverage of X and Y chromosomes, respectively.
4. The method of claim 2, further comprising:
 g) estimating the fetal fraction.
5. The method of claim 1, wherein one hypothesis is that the fetus is euploid (H0) and the other hypothesis is that the fetus is aneuploid (H1).
6. The method of claim 5, wherein the student t-statistic is calculated for both hypotheses.
7. The method of claim 6, wherein the student t-statistic is calculated for H0 and H1 according to formula: $t1_{i,j} = (cr_{i,j} - c\hat{r}_{i,j})/std_j$ and $t2_{i,j} = (cr_{i,j} - c\hat{r}_{i,j}(1+fxy_{i,j}/2))/std_j$, respectively, wherein fxy is fetal fraction.
8. The method of claim 7, wherein the log likelihood ratio of t1 and t2 is calculated according to formula: $L_{i,j} = \log(p(t1_{i,j}, \text{degree} | D))/\log(p(t2_{i,j}, \text{degree} | T))$, wherein $L_{i,j}$ is Log likelihood ratio, wherein degree refers to a t distribution degree, D refers to Diploidy, T refers to Trisomy, and $p(t1_{i,j}, \text{degree} |^*),^*=D,T$ represents conditional probability density given a t distribution degree.
9. A method to determine a fetal chromosomal abnormality, which method comprises:

a) obtaining sequence information of multiple polynucleotide fragments covering a chromosome from more than one normal samples;

b) assigning said fragments to chromosomes based on said sequence information by comparing the sequence of the fragments with a reference human genomic sequence;

c) calculating coverage depth and GC content of said chromosome based on said sequence information from said normal samples, wherein the coverage depth of the chromosome is the ratio between the number of fragments that assigns to said chromosome and the number of Reference Unique Reads of said chromosome, and the GC content of the chromosome is the average GC content of all fragments that assign to said chromosome, wherein the Reference Unique Reads are fragments of a chromosome that have unique sequences each of which is unambiguously assigned to a single chromosomal location;

d) determining the relationship between the coverage depth and GC content of said chromosome, wherein the relationship is in the formula:

$$cr_{i,j}=f(GC_{i,j})+\epsilon_{i,j}, j=1,2,\ldots,22,X,Y,$$

wherein $f(GC_{i,j})$ represents the function for the relationship between coverage depth and the corresponding GC content of sample i, chromosome j, $\epsilon_{i,j}$ represents the residual of sample i, chromosome j;

e) obtaining sequence information of multiple polynucleotide fragments from a biological sample;

f) assigning said fragments from the biological sample to chromosomes based on said sequence information from said biological sample by comparing the sequence of the fragments with a reference human genomic sequence;

g) calculating coverage depth and GC content of said chromosome based on said sequence information from said biological sample, wherein the coverage depth of the chromosome is the ratio between the number of fragments that assigns to said chromosome and the number of Reference Unique Reads of said chromosome, and the GC content of the chromosome is the average GC content of all fragments that assign to said chromosome;

h) calculating fitted coverage depth of said chromosome using said GC content of said chromosome and said relationship between coverage depth and GC content of said chromosome, wherein the fitted coverage depth is calculated according to the formula:

$$cf_{i,j}=f(GC_{i,j}), j=1,2,\ldots,22,X,Y; \text{ and}$$

i) comparing said fitted coverage depth to said coverage depth of said chromosome by a statistical hypothesis test to determine a fetal chromosomal abnormality in said biological sample, wherein the fetal chromosomal abnormality is selected from the group consisting of aneuploidy, polyploidy, monosomy, trisomy, and a sex chromosome abnormality.

10. A computer readable medium comprising a plurality of instructions for performing prenatal diagnosis of a fetal chromosomal abnormality, which comprises the steps of:

a) receiving sequence information of multiple polynucleotide fragments from a sample;

b) assigning said polynucleotide fragments to chromosomes based on said sequence information by comparing the sequence of the fragments with a reference human genomic sequence;

c) calculating coverage depth and GC content of a chromosome based on said sequence information, wherein the coverage depth of the chromosome is the ratio between the number of fragments that assigns to said chromosome and the number of Reference Unique Reads of said chromosome, and the GC content of the chromosome is the average GC content of all fragments that assign to said chromosome, wherein the Reference Unique Reads are fragments of a chromosome that have unique sequences each of which is unambiguously assigned to a single chromosomal location;

d) calculating fitted coverage depth of said chromosome using said GC content of said chromosome and an established relationship between coverage depth and GC content of said chromosome, wherein the relationship is in the formula:

$$cr_{i,j}=f(GC_{i,j})+\epsilon_{i,j}, j=1,2,\ldots,22,X,Y,$$

wherein $f(GC_{i,j})$ represents the function for the relationship between coverage depth and the corresponding GC content of sample i, chromosome j, $\epsilon_{i,j}$ represents the residual of sample i, chromosome j, and wherein the fitted coverage depth is calculated according to the formula:

$$cf_{i,j}=f(GC_{i,j}), j=1,2,\ldots,22,X,Y; \text{ and}$$

e) comparing said fitted coverage depth to said coverage depth of said chromosome by a statistical hypothesis test to determine a fetal chromosomal abnormality selected from the group consisting of aneuploidy, polyploidy, monosomy, trisomy, and a sex chromosome abnormality.

11. The computer readable medium of claim 10, further comprising:

f) determining the fetal gender.

12. The computer readable medium of claim 11, further comprising:

g) estimating the fetal fraction.

13. The method of claim 1, wherein the reference human genomic sequence is hg18 or hg19.

14. The method of claim 1, wherein the fragments that assign to more than one chromosome and the fragments that do not assign to any chromosome are disregarded.

15. The method of claim 1, wherein the relationship between coverage depth and GC content is calculated by local polynomial regression.

16. The method of claim 15, wherein the relationship is a non-strong linear relationship.

17. The method of claim 16, wherein the relationship is determined by loess algorithm.

18. The method of claim 1, further comprising:

calculating standard variation according to the formula:

$$std_j = \sqrt{\sum_i (cr_{i,j} - \hat{cr}_{i,j})^2/(ns-1)}, j = 1, 2, \ldots, 22, X, Y,$$

wherein ns represents the number of reference samples.

19. The method of claim 18, further comprising:

calculating student t-statistic according to the formula:

$$t1_{i,j}=(cr_{i,j}-cf_{i,j})/std_j, j=1,2,\ldots,22,X,Y.$$

20. The method of claim 4, wherein the fetal fraction is calculated according to the formula:

$$fy_i=(cr_{i,Y}-\hat{cr}_{i,Yf})/(\hat{cr}_{i,Ym}-\hat{cr}_{i,Yf}),$$

wherein $\hat{c}r_{i,Ym}=f(GC_{i,Ym})$ refers to the fitted coverage depth calculated from the relationship of the chromosome Y coverage depth and corresponding GC content of samples from pregnant women with a female fetus, and $\hat{c}r_{i,Ym}=f(GC_{i,Ym})$ refers to the fitted coverage depth calculated from the relationship of the chromosome Y coverage depth and corresponding GC content of male subjects.

21. The method of claim 4, wherein the fetal fraction is calculated according to the formula:

$$fx_i=(cr_{i,X}-\hat{c}r_{i,Xf})/(\hat{c}r_{i,Xm}-\hat{c}r_{i,Xf}),$$

wherein $\hat{c}r_{i,Xf}=f(GC_{i,Xf})$ is the fitted coverage depth calculated from the relationship of the chromosome X coverage depth and corresponding GC content of samples from pregnant women with a female fetus, $\hat{c}r_{i,Xm}=f(GC_{i,Xm})$ refers to the fitted coverage depth calculated from the relationship of the chromosome X coverage depth and corresponding GC content of samples from male subjects.

22. The method of claim 4, wherein the fetal fraction is calculated according to the formula:

$$fxy_i = \arg\min_{\varepsilon \in (0,1)} \left( \frac{(\hat{c}r_{i,Xf} \cdot (1-\varepsilon) + \hat{c}r_{i,Xm} \cdot \varepsilon - cr_{i,X})^2}{(\hat{\sigma}_{X,f} \cdot (1-\varepsilon))^2 + (\hat{\sigma}_{X,m} \cdot \varepsilon)^2} + \frac{(\hat{c}r_{i,Yf} \cdot (1-\varepsilon) + \hat{c}r_{i,Ym} \cdot \varepsilon - cr_{i,X})^2}{(\hat{\sigma}_{Y,f} \cdot (1-\varepsilon))^2 + (\hat{\sigma}_{Y,m} \cdot \varepsilon)^2} \right),$$

wherein $\hat{c}r_{i,Xf}=f(GC_{i,Xf})$ is the fitted coverage depth calculated from the relationship of the chromosome X coverage depth and corresponding GC content of samples from pregnant women with a female fetus, $\hat{c}r_{i,Yf}=f(GC_{i,Yf})$ refers to the fitted coverage depth calculated from the relationship of the chromosome Y coverage depth and corresponding GC content of samples from pregnant women with a female fetus, $\hat{c}r_{i,Xm}=f(GC_{i,Xm})$ refers to the fitted coverage depth calculated from the relationship of the chromosome X coverage depth and corresponding GC content of samples from male subjects, and $\hat{c}r_{i,Ym}=f(GC_{i,Ym})$ refers to the fitted coverage depth calculated from the relationship of the chromosome Y coverage depth and corresponding GC content of male subjects.

23. The method of claim 1, wherein the fetal aneuploidy is a disorder for an autosome selected from the group consisting of trisomy 13, 18 and 21.

24. The method of claim 1, wherein the fetal aneuploidy is a disorder for a sex chromosome selected from the group consisting of XO, XXX, XXY and XYY.

25. The method of claim 24, wherein the fetal gender is female, and the student t-statistic is calculated according to formula: $t1_{i,X}=(cr_{i,X}-\hat{c}r_{i,Xf})/std_{Xf}$, wherein $\hat{c}r_{i,Xf}=f(GC_{i,Xf})$ is the fitted coverage depth calculated from the relationship of the chromosome X coverage depth and corresponding GC content of samples from pregnant women with a female fetus.

26. The method of claim 25, wherein |t1| represents the absolute value of t1, wherein |t1|>3.13 indicates the fetus is XXX or XO, and wherein |t1|>5 indicates the fetus is XXX or XO.

27. The method of claim 24, wherein the fetal gender is male, and the student t-statistic is calculated according to formula: $t2_i=(cr_{i,x}-(1-fy_i/2) \cdot \hat{c}r_{i,Xf})/std_{Xf}$, wherein $\hat{c}r_{i,Xf}=f(GC_{i,Xf})$ is the fitted coverage depth calculated from the relationship of the chromosome X coverage depth and corresponding GC content of samples from pregnant women with a female fetus.

28. The method of claim 27, wherein |t2| represents the absolute value of t2, wherein |t2|>3.13 indicates the fetus is XXY or XYY, and wherein |t2|>5 indicates the fetus is XXY or XYY.

* * * * *